United States Patent
Yamashita et al.

(10) Patent No.: US 6,542,763 B1
(45) Date of Patent: Apr. 1, 2003

(54) OPTICAL MEASUREMENT EQUIPMENT AND RECORDING MEDIUM AND OPTICAL MEASUREMENT METHOD

(75) Inventors: Yuichi Yamashita, Kawagoe (JP); Atsushi Maki, Hachioji (JP); Tsuyoshi Yamamoto, Hatoyama (JP); Hideaki Koizumi, Tokyo (JP); Fumio Kawaguchi, Hinode (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/697,327

(22) Filed: Oct. 27, 2000

(30) Foreign Application Priority Data

Oct. 28, 1999 (JP) .......................................... 11-306957

(51) Int. Cl.⁷ ................................................ A61B 5/00
(52) U.S. Cl. ........................ 600/310; 600/344; 600/322
(58) Field of Search ................................ 600/309–310, 600/322–324, 373–478, 344; 356/39–42

(56) References Cited

U.S. PATENT DOCUMENTS

| | | | | |
|---|---|---|---|---|
| 4,901,564 A | * | 2/1990 | Williams et al. ............... | 73/170 |
| 5,479,934 A | * | 1/1996 | Imran ......................... | 600/544 |
| 5,803,909 A | * | 9/1998 | Maki et al. ................... | 600/310 |
| 6,334,065 B1 | * | 12/2001 | Al-Ali et al. ................ | 600/323 |

OTHER PUBLICATIONS

"Spatial and temporal analysis of human motor activity using noninvasive NIR topography" by Atsushi Maki et al. Medical Physics, vol. 22, pp. 1997 to 2005 (1995).

* cited by examiner

*Primary Examiner*—Max F. Hindenburg
*Assistant Examiner*—Matthew J Kremer
(74) *Attorney, Agent, or Firm*—Antonelli, Terry, Stout & Kraus, LLP

(57) ABSTRACT

In a system for performing imaging measurement of a test object by mounting many optical fibers to the test object, incident positions of the test object on which to illuminate light, detection positions of the test object from which to detect light and measurement positions which are determined from a positional relationship between the incident positions and the detection positions are displayed as graphic elements on a display unit. A state of detection signal level or a change in the state is displayed as a change in color or in pattern of the graphic element. Further, incident optical fibers for illuminating light to the test object and detection optical fibers for detecting light from the test object are mounted to the test object, and light emitting elements are mounted to probes to be mounted to the test object and interlocked with the change of the graphic elements.

11 Claims, 29 Drawing Sheets

● INCIDENT POSITION
○ DETECTION POSITION
□ MEASUREMENT POSITION

● INCIDENT POSITION
○ DETECTION POSITION
□ MEASUREMENT POSITION

OPTICAL MEASUREMENT EQUIPMENT AND RECORDING MEDIUM AND OPTICAL MEASUREMENT METHOD

BACKGROUND OF THE INVENTION

The present invention relates to equipment for imaging and measuring information of a light scattering object, particularly, information inside a biological body using light.

A system which can measure blood circulation, blood circulation movement and oxygen metabolism inside a biological body with a low restraint to a test object (a person to be tested) and without causing harm to the biological body is required in a field, such as clinical medicine, and also brain science. When, for example, the head is an object to be measured, the measuring of a brain disease, such as the cerebral infarction, cerebral hemorrhage and insanity, as well as the measuring of a higher level brain function, such as thinking, language and exercise can be raised as specific needs. Also, such a measured object is not limited to the head, so that preventive diagnosis in connection with heart disease, such as myocardial infarction, as used for measuring the breast, to an internal organ disease, such as kidney disease and liver disease, as well for measuring the abdomen, and further measuring of oxygen metabolism in the muscle of the hand and foot can be raised as specific needs.

In the case where the head is a measured object, in the measurement of brain disease or a higher level brain function, it is necessary to clearly specify a zone of the diseased portion or a zone of the brain function. Therefore, the imaging measurement of the brain becomes important.

Of course, the importance of imaging measurement is not limited only to the brain, but the same can be said to apply to the measurements of the beast, the abdomen and so on.

As examples, it can be mentioned that the positron emission tomography (PET) and the functional magnetic resonance imager (fMRI) and the cerebral magnetic field measurement system (MEG) are widely used in the imaging measurement of the brain function. These systems have an advantage in that an active zone inside the brain can be measured as an image, but, on the other hand, they have a disadvantage in that the systems are large in size and the operation is very complex. For example, a large dedicated room is required to install the system, and, of course, it is difficult in practice to frequently move the system. Further, the restraint to the tested person is very high, because the tested person is forced to maintain a fixed posture for a long time inside the system during measurement; and, accordingly, he or she is forced to withstand a certain amount of mental and physical pain. Furthermore, the cost required for operating the system is large because a dedicated person to maintain and manage the system is required.

On the other hand, as a method of measuring blood circulation, blood circulation movement and oxygen metabolism inside a biological body with a low restraint on the tested person and without causing harm to the biological body (non-infestation), optical measurement is very effective. The first reason is that the blood circulation and the oxygen metabolism in a biological body correspond to a concentration and a change in the concentration of a specific pigment (hemoglobin, cytochrome, myoglobin etc.) in the biological body, and the concentration of the pigment can be measured from an amount of absorption of light having wavelengths within a range from visual to infrared light. The blood circulation and the oxygen metabolism are indicative of a normal or abnormal condition of the organ in the biological body and further indicate activity of the brain in regard to a higher level brain function. In addition, the second reason for the effectiveness of optical measurement is that the system can be made small in size and the measurement can be easily performed because of the technological development of laser diodes, light emitting diodes and photodiodes. Further, the fixing of the head during measurement becomes unnecessary by employing highly flexible optical fibers in the measurement, and, accordingly the restraint of the tested person can be largely reduced and the mental and physical pain endured by the tested person can be largely reduced. Furthermore, the third reason is that the optical measurement does not cause harm to the biological body when using light having an intensity within a safety standard range.

In addition to the advantages described above, the optical measurement has advantages of real time measurement, quantification of pigment concentration in a biological body and so on which the PET, the fMRI and the MEG do not have. In making use of these advantages of the optical measurement, systems which measure the inside of a biological body by illuminating light having wavelengths within a range from visual to infrared light onto the biological body and detecting reflected light from the biological body are disclosed, for example, in Japanese Patent Application Laid-Open No. 57-115232 and Japanese Patent Application Laid-Open No. 63-275323. Further, systems for imaging a biological body using optical measurement are disclosed in Japanese Patent Application Laid-Open No. 7-79935, Japanese Patent Application Laid-Open No. 9-19408 and Japanese Patent Application Laid-Open No. 9-149903. Furthermore, the effectiveness of the imaging measurement on a biological body using light is described, for example, in an article entitled "Spatial and temporal analysis of human motor activity using noninvasive NIR topography", by Atsushi Maki et al., Medical Physics, Vol. 22, pages 1997 to 2005 (1995).

In the non-invasive imaging measurement of a biological body using light, it is necessary to illuminate light beams onto a plurality of positions and to detect light beams from a plurality of positions. In that case, in order to further improve the optical measurement so that it is higher in accuracy and higher in sensitivity, additional circuits, such as a modulation adding, a modulation measuring, a temperature control, an optical intensity control, and temperature compensating circuits are necessary for the opt-semiconductor elements, such as a laser diode and a photodiode. Therefore, it is difficult to mount such an opt-semiconductor element directly on the test object. In order to make such measurement practically possible, light illumination and light detection using many optical fibers are required. However, Japanese Patent Application Laid-Open No. 7-79935 does not disclose in what arrangement each of the plurality of optical fibers used for the measurement is mounted on the test object in order to perform the desired image measurement.

On the other hand, in Japanese Patent Application Laid-Open No. 9-19408 and Japanese Patent Application Laid-Open No. 9-149903 and the cited article in Medical Physics, methods of efficiently arranging optical fibers on a test object are disclosed in detail. According to these methods, assuming that a square area having a side of 6 cm in the head is measured as a limited zone, four incident optical fibers for each of four incident positions and five detecting optical fibers for each of detection positions, that is, nine optical fibers in total, are necessary. Therefore, since the measurement position is a midpoint between the incident position and the detection position adjacent to each other, twelve measurement positions in total are set. In the field of the clinical medicine and the brain science, it is required to measure brain activity in a wide region. When a square area having a side of 12 cm is intended to be measured by applying the above-mentioned method of arranging the incident positions and the detection positions, twelve incident optical fibers and thirteen detecting optical fibers, that is, twenty-five optical fibers in total are necessary. When the measured area is further expanded, the number of optical fibers to be mounted is further increased and exceeds 100 depending on the circumstances. The prior art described above shows a part of the measurement principle in the non-invasive imaging measurement of a biological body using light, but does not disclose any display nor any function for the operator to efficiently mount the optical fibers.

When a large number of optical fibers are mounted onto a test object, the optical fibers can not be arranged on the test object in random. Firstly, at least, it is necessary that the incident optical fibers connected to light sources are mounted at the incident positions and the detecting optical fibers connected to photodetectors are mounted at the detection positions. Further, a correct image can not formed unless information on the light from which light source is incident to which position of the test object and on which detector detects light from which position of the test object is made clear for each of the incident and the detecting optical fibers. Therefore, the optical fibers to be mounted to all the incident positions and the detection positions need to be uniquely determined. When the number of optical fibers to be mounted is several tens to one hundred, it is difficult for the operator to speedily perform the work by correctly judging which optical fiber is to be mounted to which position of the test object. For example, if the operator works while finding the optical fiber for each of the positions to be connected one by one, it takes quite a long time to connect all the optical fibers. Accordingly, not only will the efficiency of measurement be decreased, but both the operator and the test object (the test person) will be physically and mentally exhausted. From the above, the first problem to be solved by the present invention is to provide an imaging measurement system which is non-invasive to a biological body using light which is capable of efficiently mounting many optical fibers.

The second problem to be solved by the present invention is to improve the reliability in the imaging measurement mounting many optical fibers. A system for efficiently displaying a state of a detection signal level which influences the reliability and for efficiently displaying the change in the state is provided. An example of the second problem will be described below.

The system described in Japanese Patent Application Laid-Open No. 9-149903 simultaneously performs a multichannel measurement of plural positions and plural wavelengths necessary for the imaging measurement of a concentration change in the pigment contained in a biological body, such as hemoglobin and the like. The simultaneous measurement is necessary for biological body measurement, particularly, for brain function measurement, in order to attain a high resolution over time. The outline of the system described in Japanese Patent Application Laid-Open No. 9-149903 is shown in FIG. 4. In this system, light is incident on a test object from a plurality of incident position s at the same time, and light is detected at a plurality of detection positions at the same time. Although the technique of measurement of plural wavelengths is omitted in FIG. 4, the measurement of plural wavelengths can be realized by applying the construction of this system in principle. In that case, the intensity of the light is modulated by a different frequency for each of the incident positions. For example, the modulation frequencies of the light incident on the incident positions 1, 2, 3 and 4 in FIG. 4 are f1, f2, f3 and f4. Therefore, each of these modulation frequencies is positional information corresponding to each of the incident positions. Although the light detected at the detection position 1 contains modulated light, the optical measured signal in regard to the positional information can be separately measured by measuring each of the modulation frequency signals selectively from the light output from the photodiode using a filter circuit, such as a lock-in amplifier or the like. For example, letting the detection signal levels be I1, I2, I3 and I4 for the modulations f1, f2, f3 and f4 detected by the photodiode corresponding to the detection position 1, respectively, each of the signals in the outputs of the lock-in amplifiers in synchronism with the individual frequencies is completely separated. As a result, efficient multichannel simultaneous measurement can be realized without interference between the signals, that is, without cross talk.

However, when an image is finally obtained from such measurement, a high accuracy of measurement is required for each of the signals. For example, if there is a signal having a very low measuring accuracy, that is, a very low S/N ratio, the reliability of a measurement position on the image corresponding to the signal is largely decreased. Thereby, the reliability of the image itself is also decreased. Therefore, a high accurate measurement having a good balance in S/N ratio over all the detection signals is required. However, the conventional system has the following problem in regard to the measuring accuracy.

In general, the state inside a biological body is optically heterogeneous. When the incident position or the detection position is placed in a portion having a large amount of hemoglobin of light absorbent material, such as a large blood vessel, attenuation of light becomes large and the corresponding detection signal level is largely reduced. The other causes which reduce the signal level in a specific measurement channel, as described above, are a case where the end surface of the optical fiber used for the measurement is optically stained; a case where the optical fiber is damaged, for example, the optical fiber is broken at a midpoint; and a case where there exists a problem in the state of mounting the optical fiber, for example, where hair comes between the optical fiber and the skin of the person to be tested.

Description will be made below on how the N/S ratio of the measurement is affected when a part of the detection signal level is largely decreased, and there is an unbalance in the detection signal levels as a whole.

In general, a shot-noise of a photodetector, such as a photodiode, is in proportion to the square root of the total amount of light arriving at the detector, that is, the total sum of the detected optical intensities. Here, it is assumed that of the detection signal levels I1, I2, I3 and I4 measured at the detection position 1 in FIG. 4, the detection signal levels I1, I2 and I3 are nearly equal (I1~I2~I3) and only the detection signal level I4 is smaller than the others by 1 order (I1>>I4). This situation is assumed for a case where there is a blood vessel at a position near the incident position 4 or a case where there is a problem in mounting the optical fiber at the incident position 4. In this case, the noise detected by the photodiode is mainly in proportion to the square root of the total sum of the detected intensities (I1+I2+I3+I4).

Therefore, the originally low signal level of I4 is largely reduced in S/N ratio by being strongly affected by the strong signal levels of I1, I2 and I3. In order to describe this phenomenon further in more detail, a case is considered in which the signal level of I4 is not changed and the signal levels of I1, I2 and I3 are further increased. In this case, in regard to I4, the signal level, that is, S, is not changed, but the noise level N is increased. As a result, the S/N ratio of the signal in regard to I4 is further deteriorated. On the other hand, the S/N ratios in regard to the strong signal levels of I1, I2 and I3 are improved. Therefore, when a plurality of light signals are detected by a single photodetector, a large difference in the S/N ratio is caused among the measured signals.

In addition to this, the following problem occurs in the measurement performed by this method. In a case where many strong detected light signals, for example, such as the signals I1, I2 and I3 described above, are contained in a detection signal, because of the limitation of the dynamic range of the detector, such as a photodetector and a lock-in amplifier, there are some cases where the total sum of the detected light signals exceeds the dynamic range. The dynamic range is specified by a range in which the linear response property of the measurement equipment is guaranteed. However, even if the signal level exceeds the dynamic range, a finite value is sometimes output from the detector. However, the value in that case is very low in the reliability of the measurement.

As described above, when a large difference occurs between the detection signal levels, the S/N ratio of each of the signals becomes large. When an image is formed using these signals, the reliability of the image is decreased. In the case where there is a strong detected light signal among these signals, the detected light signal exceeds the dynamic range of the detector, thereby to deteriorate the reliability of the measurement itself.

The second problem to be solved by the present invention is to provide a highly reliable measurement system to effect multichannel simultaneous measurement of plural positions and plural wavelengths, which realizes a high time-resolution in the non-infestation imaging of a biological body using light. In the case where there is a cause for unbalance of the measured signals resulting in a decrease of the reliability, such as a stain or a damage in the optical fiber or a problem in the mounting state of the optical fiber, it is generally very difficult to find the corresponding fiber and the corresponding position among the large number of several tens to about 100 mounted optical fibers. Therefore, the second object of the present invention is to provide a system which makes it easy for the operator to solve the problem of mounting the optical fibers by easily, clearly and effectively displaying the corresponding optical fiber, when there is the problem in an optical fiber or in the mounting state of an optical fiber.

The third problem to be solved by the present invention is to always maintain the high reliability of the measurement even during the measurement.

There are some cases where the detection signal level is largely changed during measurement, for example, of a person's head, due to a large physiological change, such as a change in a blood flow rate or due to occurrence of sudden displacement of a probe mounting the optical fiber. When the detection signal level exceeds the appropriate dynamic range of the measurement equipment as a result, the effectiveness of the measurement may be lost. Further, since there are some cases where it is difficult to repetitively perform a measurement depending on the physiological state of a test body, it is necessary to perform and complete the measurement with a high reliability once the measurement is started. The third problem to be solved by the present invention is to provide a system capable of solving the above-mentioned need.

SUMMARY OF THE INVENTION

In order to solve the first problem described above, in regard to incident positions of light on a test object and detection positions of light from the test object and measurement positions determined by spatial arrangement between the incident positions and the detection positions, a relative positional relationship among the positions and a state of detection signals or a change in the state are displayed on a display unit. On the display unit, the incident positions, the detection positions and the measurement positions are individually displayed by graphic elements, and these graphic elements are arranged in a specified frame-shaped picture. In this regard, the state of the detection signals or a change of the state or a fluctuation per unit time of the state is displayed so as to be identified by a changing color or pattern of the graphic elements on the display unit. This identification display method is specific to the non-invasive imaging measurement of a biological body using light. Further, the optical measurement system comprises an optical illuminating means to illuminate the test object, an optical detection means for detecting light returned from the test object, and display elements in probes to mount these means on the test object, and the display elements are operated in an interlocking manner with the display of the graphic elements on the display unit. Further, in order to make it possible for an operator to easily understand the spatial arrangement of the incident positions and the detection positions and the measurement positions, graphic elements expressing the incident positions and the detecting positions and the measurement positions are displayed by superposing the graphic elements on an image representing a shape of the test object or information on an inside portion of the test object.

Further, in order to solve the second problem, prior to performing the regular measurement involving multichannel simultaneous measurement at a plurality of positions and with a plurality of wavelengths, as a preparation for the measurement, light is sequentially incident on the test object for each of the incident positions and for each of the wavelengths, and signal levels of the detection light are measured for each of the incident positions and for each of the wavelengths. Further, the amplification factor of each of the amplifiers and each of the optical intensity levels are independently changed for each of the incident positions and for each of the wavelengths so that each difference between the detection signal levels measured for each of the incident positions and for each of the wavelengths may fall within an appropriate range. The amplification of each of the signal levels or each of the optical intensity levels is changed so that the total sum of the detection signal levels relating to each of the measurement instruments may fall within an appropriate range.

When light is illuminated as the preparation measurement for each of the incident positions or for each of the wavelengths, each incident optical intensity is continuously increased from the zero level up to a set intensity level, and the detection signal level relative to the change in the optical intensity is continuously detected. At that time, when the response of the detection signal level to the incident light intensity level becomes non-linear, the incident light intensity level is decreased to a set level. In the course of the preparation measurement, when the detection signal level is out of the appropriate range, the corresponding incident position and the corresponding detection position and the corresponding measurement position are shown by a change in color or pattern of the graphic elements on the display unit. In addition, the corresponding incident position and the corresponding detection position are also displayed in the display elements of the optical illuminating means and the optical detection means and the probe.

Further, in order to solve the third problem, when the detection signal level is out of the appropriate range in the regular measurement performing process for measurement of a pigment, such as hemoglobin, in a biological body, the corresponding incident position and the corresponding detection position and the corresponding measurement position are displayed by a change in color or pattern of the graphic elements on the display unit. Further, the corresponding incident position and the corresponding detection position are also displayed in the display elements of the optical illuminating means and the optical detection means and the probe. When the detection signal level is further out of the appropriate range, the amplification factor of the amplifier relating to the detection signal or the optical intensity level of the corresponding incident light is automatically changed at a set rate.

In the solutions of the problems described above, programs for executing the display and the measurement described above are recorded in a computer-readable recording medium.

DESCRIPTION OF THE PREFERRED EMBODIMENTS

An embodiment of the present invention will be described in detail below.

Figure 5:
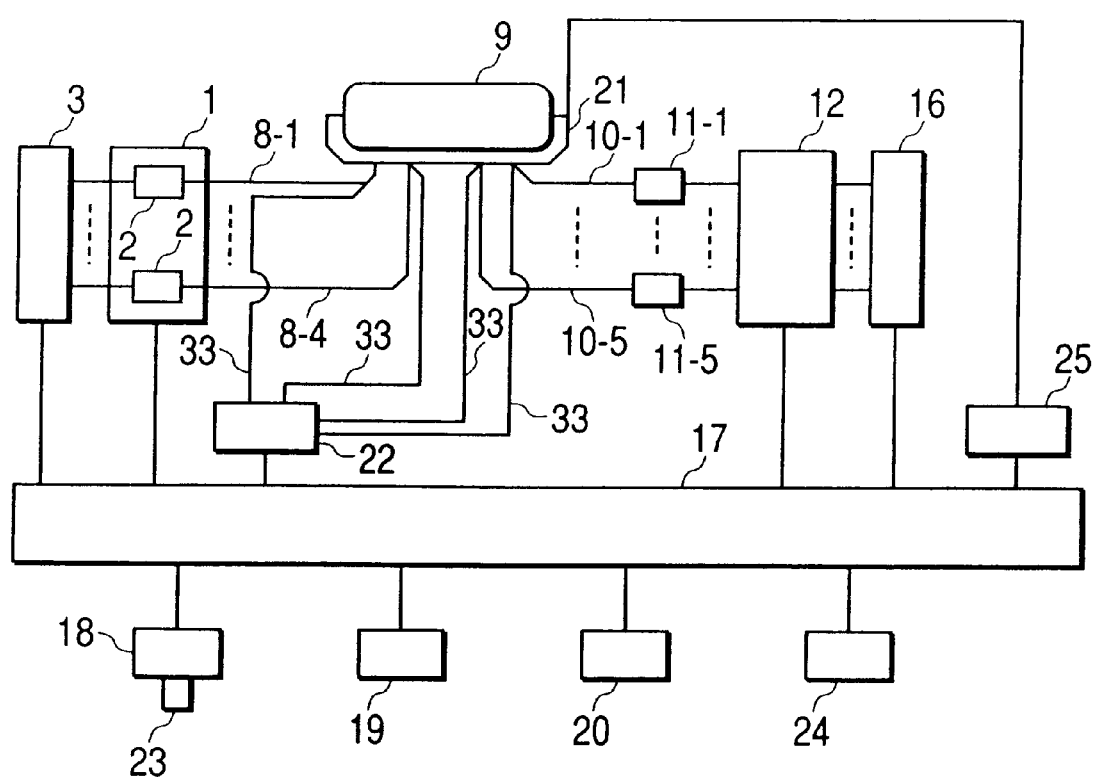
FIG. 5 is a block diagram showing the basic structure of an embodiment of a system in accordance with the present invention.

FIG. 5 is a block diagram showing the basic structure of an embodiment of an optical measurement system in accordance with the present invention. This embodiment represents a case where, for example, the inside of a cerebrum is imaged by illuminating and detecting light onto and from the head of a person, and is performed using four incident optical fibers (four incident positions), five detection optical fibers (five detection positions) and twelve measurement channels, that is, twelve measurement positions. The number of the incident and detection positions is selected as an example for concisely showing the key point of the present invention, and, of course, it is possible to apply the present invention to a case where the total number of the optical fibers exceeds, for example, 100. In addition, the present invention can be applied to the other portions of a biological body than the head as the object to be measured, and further, to a liquid, a solid or a gas other than a biological body.

A light source 1 is composed of four light modules 2. Each of the light modules is composed of laser diodes emitting light having a plurality of wavelengths within the range of visual wavelength to infrared wavelength, for example, two laser diodes respectively emitting light having two wavelengths of 780 nm and 830 nm. The value of the two wavelengths are not limited to 780 nm and 830 nm, and the number of the wavelengths is not limited to two wavelengths. In regard to the light source 1, a light emitting diode may be used instead of a laser diode. Optical intensities emitted by all of the eight laser diodes included in the light source 1 are modulated by an oscillator unit 3 composed of eight oscillators having different oscillation frequencies, respectively.

Figure 6:
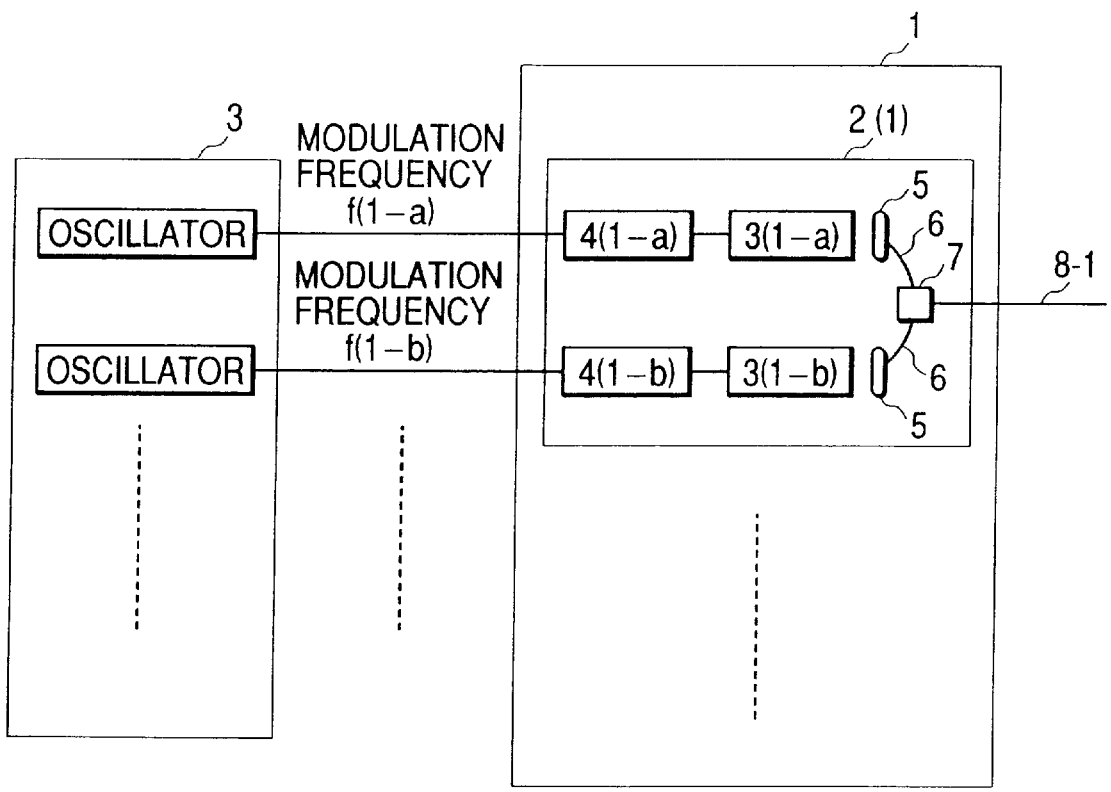
FIG. 6 is a block diagram showing the structure of an optical module in the embodiment.
Figure 7:
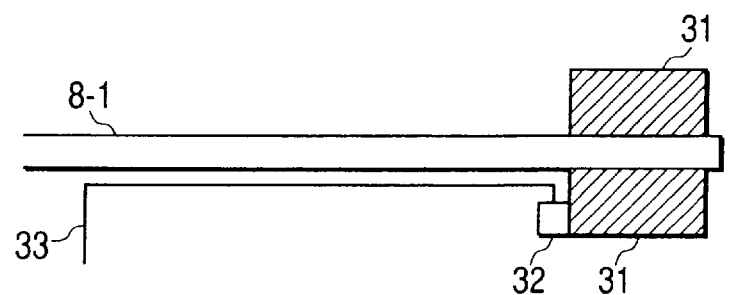
FIG. 7 is a sectional view showing the structure of a top end of an optical fiber in the embodiment.
Figure 8:
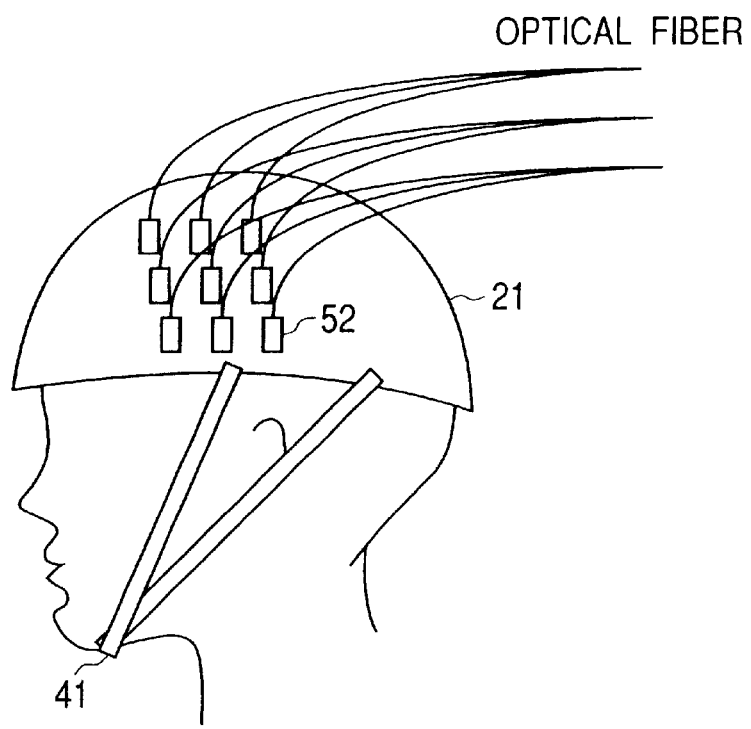
FIG. 8 is a diagram showing the mounting state of probes in the embodiment.
Figure 9:
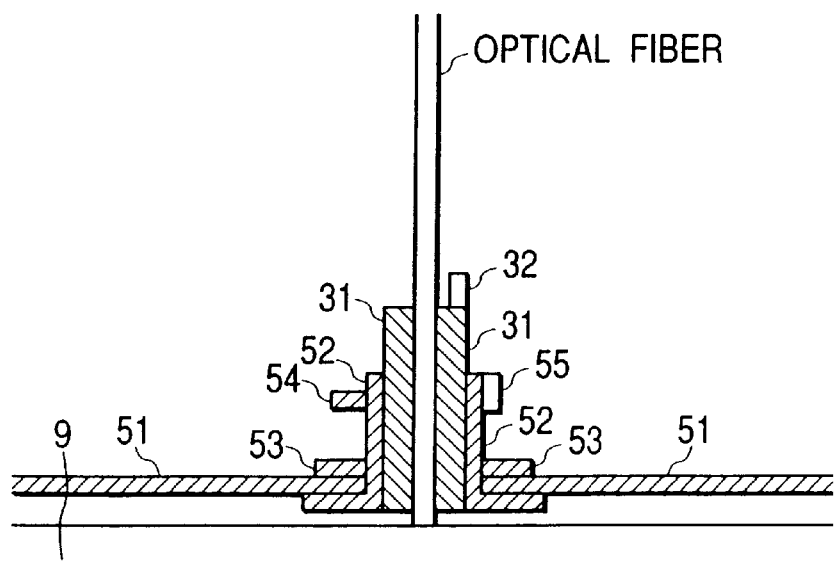
FIG. 9 is a sectional view showing the construction of the probe and the optical fiber under a mounting state in the embodiment.

Here, the configuration of the optical module 2 will be described taking the optical module 2 (1) as an example, referring to FIG. 6. In the optical module 2 (1), there are included laser diodes 3(1-a), 3(1-b) and drive circuits 4(1-a), 4(1-b) for the laser diodes. As for the characters in the parentheses, the numeral expresses the optical module in which the laser diode or the drive circuit is contained, and the letters a and b are symbols expressing wavelengths 780 nm and 830 nm, respectively. The laser diode drive circuits 4(1-a) and 4(1-b) apply DC bias currents to the laser diodes 3(1-a) and 3(1-b), and the oscillators 3 apply voltages of frequencies f(1-a) and f(1-b) to the laser diodes 3(1-a) and 3(1-b) to modulate light emitted from the laser diodes 3(1-a) and 3(1-b), respectively. Although the modulation in the embodiment is analogue modulation using sinusoidal waves, digital modulation using rectangular waves different in time interval from each other may be used. These light beams are incident to optical fibers 6 through condenser lenses 5 individually in each of the laser diodes. The light beams of two wavelengths individually incident to the optical fibers are introduced into one optical fiber, for example, into an incident optical fiber 8-1 through an optical fiber coupler 7, individually in each of the optical modules. The light beams of two wavelengths are introduced from the incident optical fiber 8-1 into an optical fiber 8-4 individually in each of the optical modules. The structure of the optical fiber is shown in FIG. 7, taking the incident optical fiber 8-1 as an example. There is an optical fiber support portion 31 at the top end of the incident optical fiber 8-1, and a display element 32 is mounted on the support portion 31. A light emitting diode (LED) may be used as the display element. A thin electric signal cable 33 is arranged in parallel to the optical fiber 8-1. The optical fiber has a diameter of, for example, about 1 mm, and the electric signal cable has a diameter of, for example, about 0.1 mm. A probe 21 is used for illuminating light from the optical fibers to a test object 9. The probe, for example, has a helmet shape or a cap shape as shown in FIG. 8. The probe 21 has a base formed of, for example, a thermoplastic resin sheet having a thickness of about 2 mm. The probe is mounted onto the test object using, for example, an elastic cord 41. The structure of the probe will be described, referring to FIG. 9. Holes are formed in the probe base 51 at individual positions for illuminating and detecting light to and from the test object. Optical fiber holders 52 are arranged in the holes. The optical fiber holder 52 comprises a hollow holder main body 52, a nut 53, and an optical fiber support portion fixing screw 54. By inserting the optical fiber and the optical fiber support portion into the inside of the holder 52, the end surface of the optical fiber is brought lightly in contact with the surface of the test object and is then fixed in position by the fixing screw 54. Further, the display element 55 is mounted on the optical fiber holder 52. An LED may be used as the display element.

Light is illuminated from the four different incident positions onto the surface of the test object 9 by the incident optical fibers. Light reflected from the test object is detected by detection optical fibers 10-1 to 10-5 arranged at five detection positions on the surface of the test object. The structure of the top end of the detection optical fiber also has an optical fiber support portion and a display element, similar to the structure of the incident optical fiber. The detection optical fiber is also fixed to the optical fiber holder 52 in the probe 21, similar to the incident optical fiber.

Figure 1:
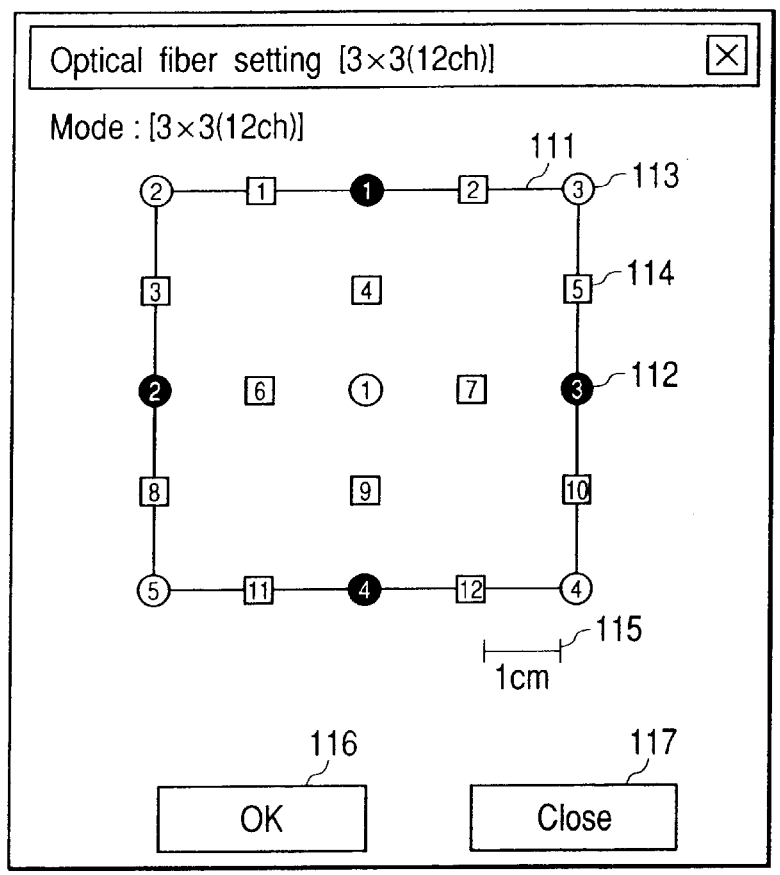
FIG. 1 is a diagram showing the structure of an example of a basic window in an embodiment in accordance with the present invention.
Figure 2:
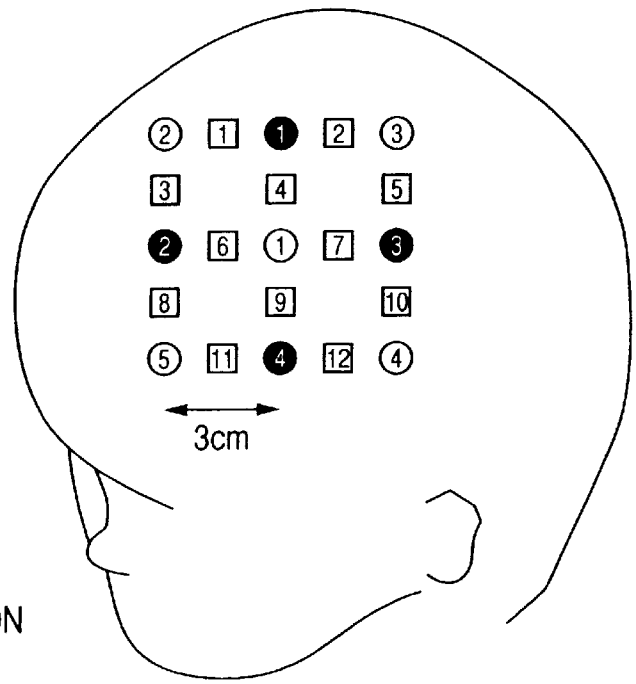
FIG. 2 is a diagram showing an example of arrangement of incident positions and detection positions for 12-channel measurement.

Here, an example of the geometrical arrangement of the incident positions 1 to 4 and the detection positions 1 to 5 on the surface of the test object is shown in FIG. 1 and FIG. 2. In this embodiment, the incident position and the detection position are alternatively arranged in a square lattice layout. Therein, when it is considered that the midpoint between the incident position and the detection position adjacent to each other is a measured position, the number of the measurement positions, that is, the number of measurement channels is twelve because there are twelve combinations of the incident position and the detection position adjacent to each other. This optical incident/detection position arrangement is described, for example, in Japanese Patent Application Laid-Open No. 9-149903 and an article entitled "Near-infrared topographic measurement system: Imaging of absorbers localized in a scattering medium", by Yuichi Yamashita et al., Review of Scientific Instrument, Vol. 67, pages 730–732 (1996). When the distance between the incident position and the detection position adjacent to each other is set to 3 cm, the light detected at each of the detection positions carries information on the cerebrum as a result of having passed through the skin and the cranium. This fact is described, for example, in an article entitled "Intracerebral penetration of infrared light", by P. W. McCormic et al., Journal of Neurosurgery, Vol. 76, pages 315–318 (1992).

Figure 3:
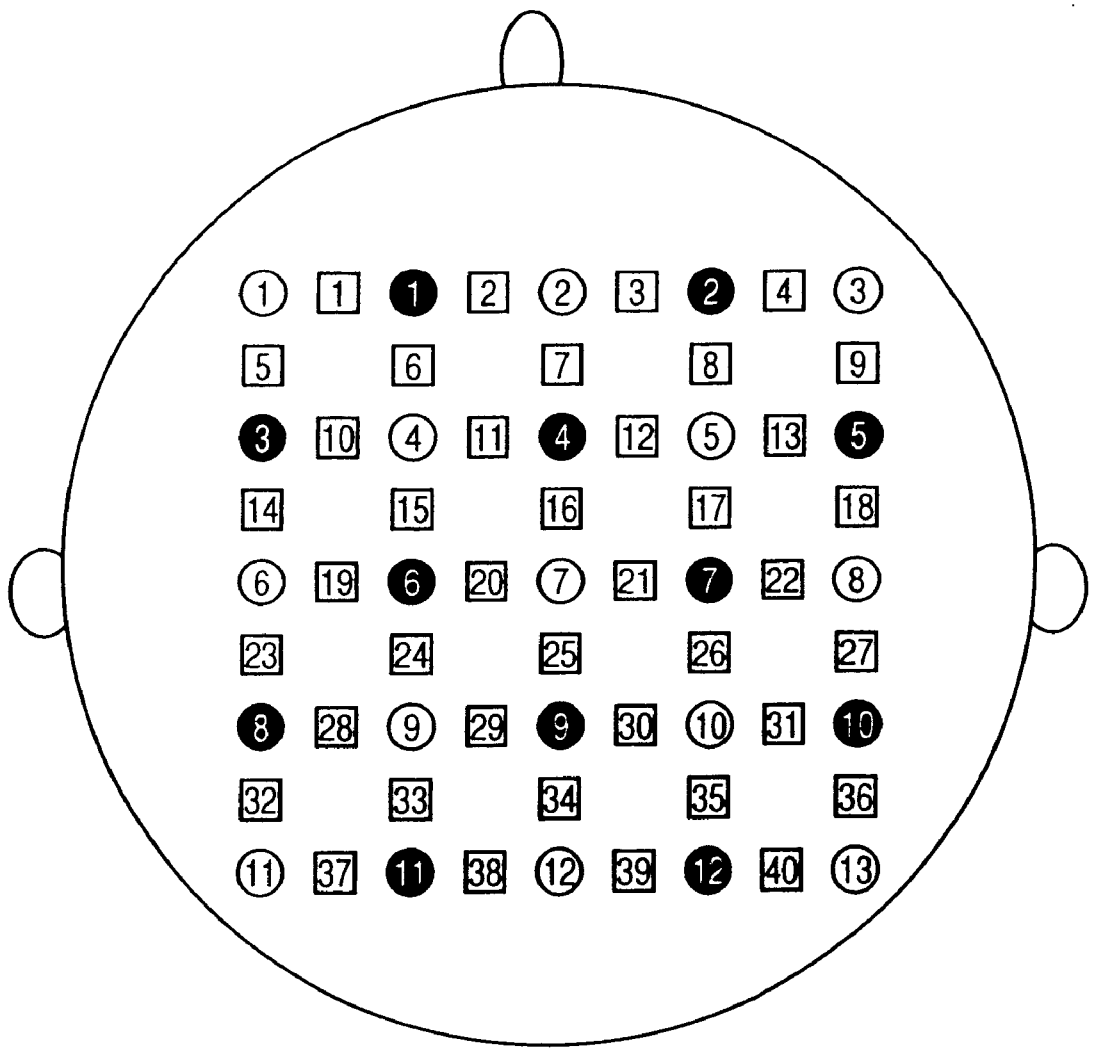
FIG. 3 is a diagram showing an example of arrangement of incident positions and detection positions for 40-channel measurement.
Figure 4:
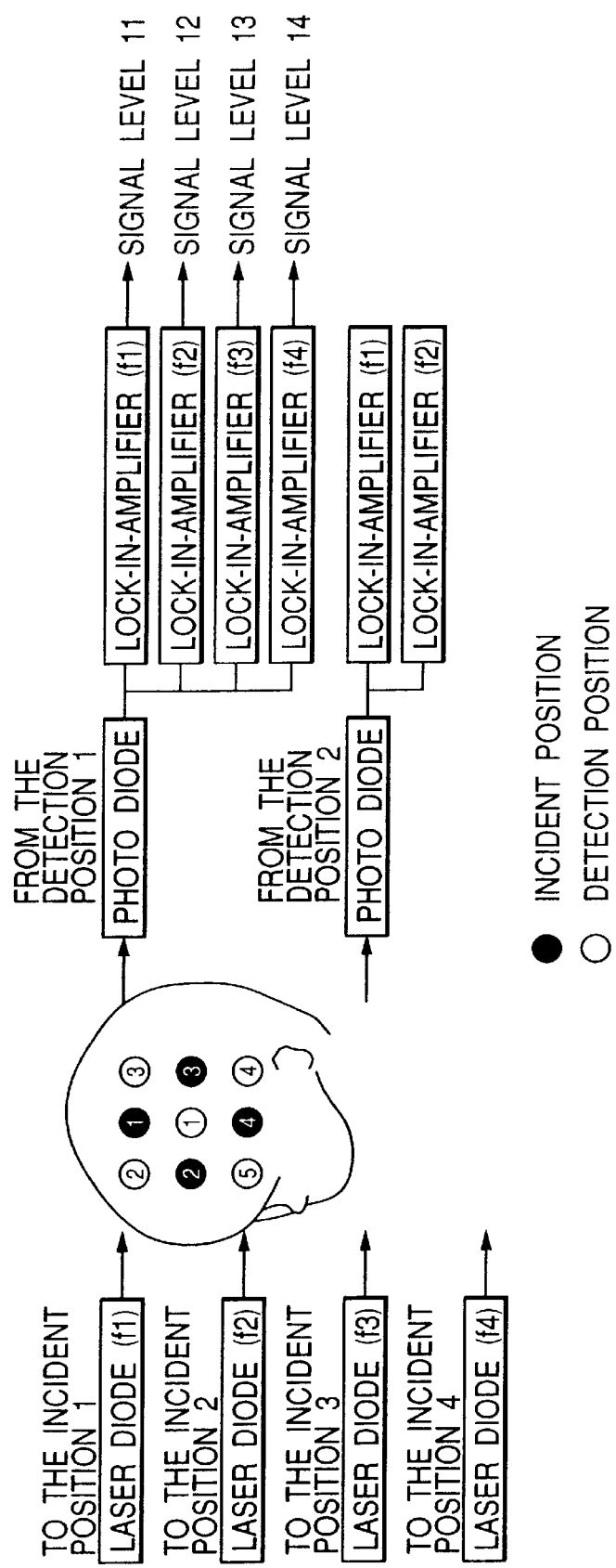
FIG. 4 is a diagram showing the key-point outline of a conventional high time-resolution measurement system.

From the above, by setting twelve measurement channels in this arrangement of the incident and detection positions, the measurement of the cerebrum in the area of 6 cm by 6 cm can be performed as a whole. Although this embodiment shows the case of twelve measurement channels for the purpose of simplification, it is possible to easily increase the number of measurement channels and expand the measurement area by further increasing the number of incident positions and detection positions arranged in the lattice layout. For example, FIG. 3 shows an arrangement for forty channels. Further, the arrangement of the incident and the detection positions is not limited to a square lattice shape, and the distance between the incident position and the detection position adjacent to each other is not limited to 3 cm. The arrangement shape and the distance may be arbitrarily changed depending on the measurement position or the like.

Referring to FIG. 5, the reflected light captured by each of the detection optical fibers 10-1 to 10-5 is independently detected by five photo-detectors, for example, photodiodes 11-1 to 11-5, individually in each of the detection optical fibers. It is preferable that an avalanche photodiode capable of performing highly sensitive photo-measurement is used for the photodiode. Further, a photo-multiplier tube may be used as the photo-detector. After the light signals are converted into electric signals by the photodiodes, the modulation signals corresponding to the incident position and to the wavelengths are selectively detected by a lock-in amplifier module 12, which is composed of circuits for selectively detecting the modulation signals, for example, a plurality of lock-in amplifiers. Although the lock-in amplifier is shown as a modulation signal detecting circuit capable of coping with analogue modulation in this embodiment, a digital filter or a digital signal processor may be used for detecting the modulation signal when digital modulation is used.

Figure 10:
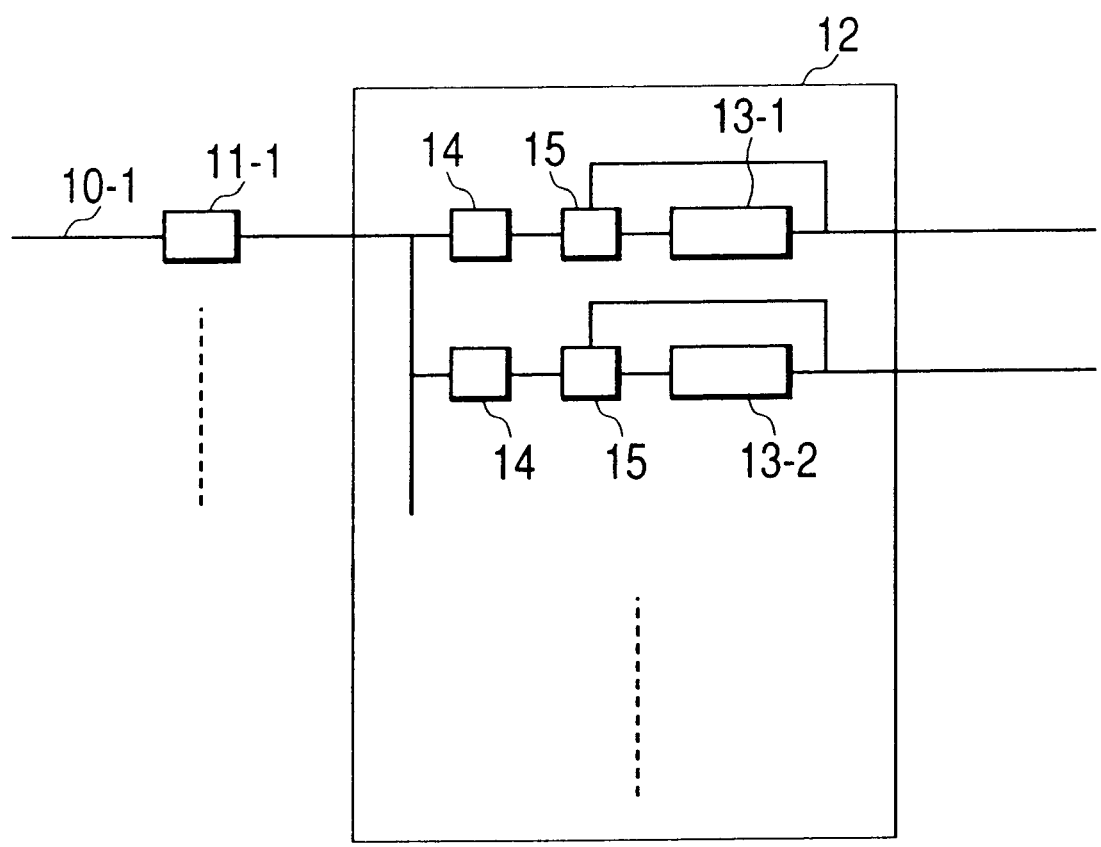
FIG. 10 is a block diagram showing the structure in a lock-in amplifier in the embodiment.

A detailed example of the process of separation of the modulation signals will be described, with reference to the detection signal in the "detection position 1" in FIG. 2, that is, the detection signal by the photodiode 11-1. Here, explanation will be made using the diagram of the lock-in amplifier module 12 shown in FIG. 10. In the "detection position 1", light incident on the "light incident position 1", the "light incident position 2", the "light incident position 3" and the "light incident position 4", that is, the "measurement position 4", the "measurement position 6", the "measurement position 7" and the "measurement position 9" are objects to be measured. There, the light detected by the photodiode 11-1 contains eight signals having modulation frequencies of f(1-a), f(1-b), f(2-a), f(2-b), f(3-a), f(3-b), f(4-a) and f(4-b) corresponding to light of two wavelengths individually incident on the "incident position 1", the "incident position 2", the "incident position 3" and the "incident position 4". Therefore, the output signal of the photodiode 11-1 is distributed to eight positions, and they each are measured by eight lock-in amplifiers 13-1 to 13-8 which individually use the eight modulation frequencies as reference signals. The input signal to each of the lock-in amplifiers passes through an amplifier 14 and a switch 15. There, since the reference signal of, for example, the lock-in amplifier 13-1 is f(1-a), only light having the wavelength of 780 nm incident on the "incident position 1", that is, only the light having the optical modulation frequency of f(1-a) can be selectively detected of the light detected by the photodiode 11-1.

Similarly, in each of the other lock-in amplifiers, the light incident on the specified incident position and having the specified wavelength can be selectively detected. Similarly, in regard to the light detected at the other detection positions, that is, the detection signals from the other photodiodes 11-2 to 11-5, detection light amounts to all the measurement positions and all the wavelengths can be simultaneously measured by individually performing lock-in detection of the modulation frequencies corresponding to the adjacent incident position and the wavelength. In the case of using twelve measurement positions and two wavelengths, as in this embodiment, the number of signals to be measured is twenty-four. Therefore, the lock-in amplifier module 12 contains twenty-four lock-in amplifiers.

Figure 11:
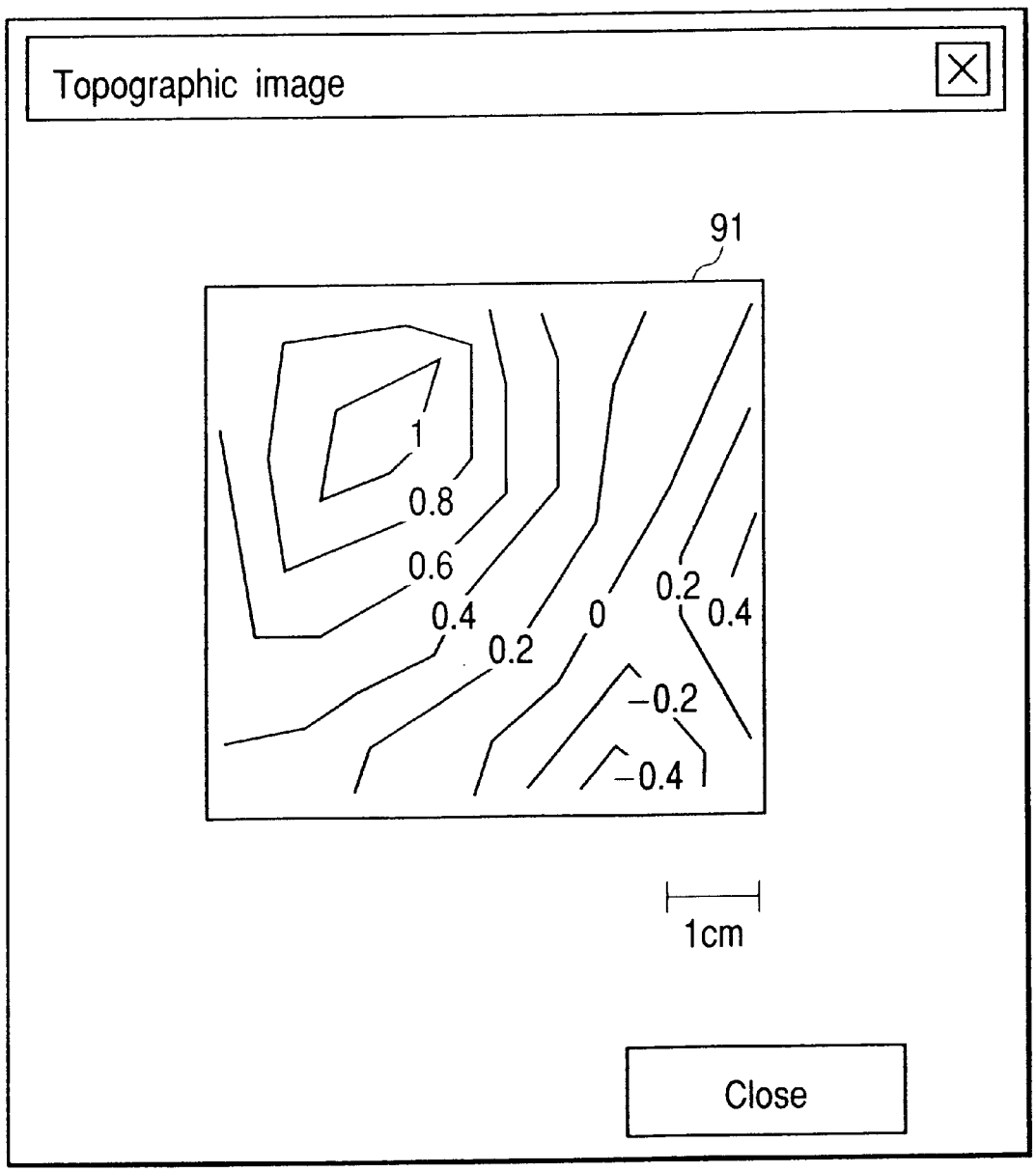
FIG. 11 is a diagram showing an example of the display of a measurement result in the embodiment.

The analogue output signals from the lock-in amplifiers 13-1 to 13-24 are individually converted into digital signals by a 24-channel analogue-to-digital converter 16. The measurement is controlled by a control unit 17. Further, the measured signals are recorded in a recording unit 18. Further, in a processing unit 19, a change of oxygenated hemoglobin concentration and a change of deoxygenated hemoglobin concentration attended with cerebrum activity, and further a change of total hemoglobin concentration as the sum of these hemoglobin concentrations, are measured using the detected light amount of each of the measurement positions and each of the wavelengths of the recorded signals. In regard to the measurement method and the imaging method, the methods described, for example, in Japanese Patent Application Laid-Open No. 9-19408 and in an article entitled "Spatial and temporal analysis of human motor activity using noninvasive NIR topography", by Atsushi Maki et al., Medical Physics, Vo. 22, pages 1997–2005 (1995) are used. The obtained image is displayed on the display unit 20. The image produced by the display unit 20 may be a contour map as shown in FIG. 11, or a gray-scale image, a color identifying image, or a three-dimensional perspective image.

Therein, the control unit 17 and the processing unit 19 may be integrated into a personal computer. Further, the recording unit 18 is composed of a memory, a hard disk and various kinds of memory drives, such as a floppy disk drive and so on, which are included as part of the personal computer. It is possible to access the recording unit 20 by a recording medium 23, such as a floppy disk or the like. A monitor forming part of the display unit 20 may be a CRT display or a liquid crystal display. Further, an operating unit 24 is connected to the control unit 17, and the operating unit 24 includes a keyboard and a mouse and the like, which input and output various kinds of information and perform adding and deleting of data. The control unit 17 controls an optical fiber display controller 22 for controlling display elements included in the optical fiber support portions and a probe display controller 25 included in the optical fiber holder of the probe.

Figure 12:
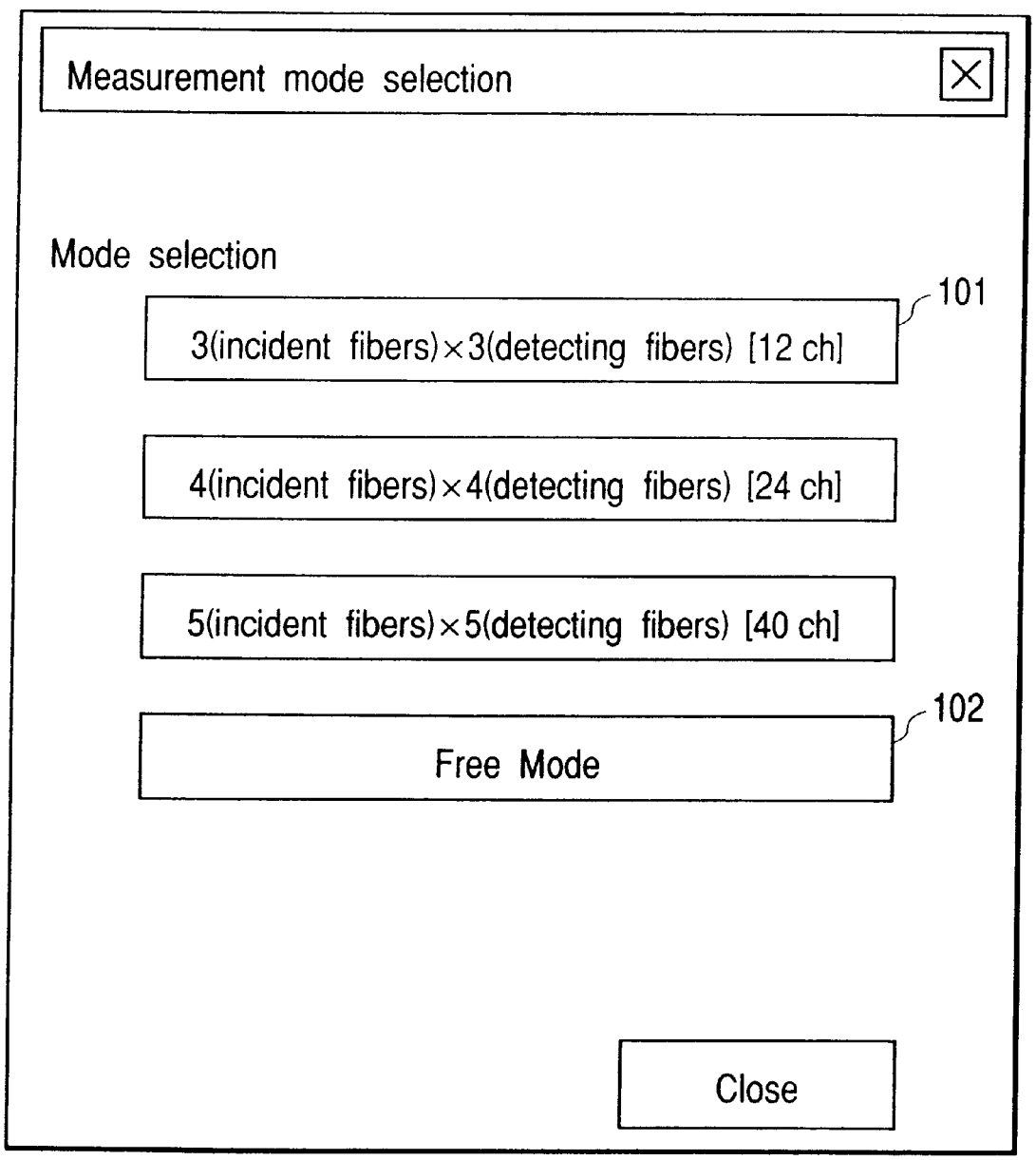
FIG. 12 is a diagram showing an example of a measurement mode selection window in the embodiment.

Here, a procedure for mounting many optical fibers onto the head before initiating the measurement will be described. Prior to mounting, a measurement arrangement (optical fiber arrangement) mode selection window, such as shown in FIG. 12, is displayed on the display unit 20. Therein, in addition to some established modes prepared as programs on optical fiber arrangement, selection of a free mode (102) is also available. In the free mode selection, the arrangement of the incident positions and the detection positions can be freely set.

Referring to FIG. 12, when the 12 channel mode (101) is selected, an optical fiber mounting image as shown in FIG. 1 is displayed. In this image, some number of display elements are arranged inside, for example, a large quad-rangle frame-shaped image (111). Here, an arranging position for the incident optical fiber is shown by a black circular graphic element (112); an arranging position for the detection optical fiber is shown by a white circular graphic element (113); and the measurement position is shown by a quadrangular graphic element (114). Although it is preferable that the relative arrangement of the graphic elements is closely similar to the actual arrangement of the optical fibers, the similarity is not always necessary. A symbol expressing an optical fiber number, for example, a numeral corresponding one-to-one to the incident position or the detection position is written in the inside of each of the graphic elements. In order to clearly distinguish among the graphic elements at the incident position, the detection position and the measurement position, the incident position number may be displayed in red color, the detection position number may be displayed in blue color and the measurement position number may be displayed in black color. Of course, each of the graphic elements and each of the numbers used here are not limited to these colors or shapes. Further, in the arrangement of each of the display elements, a scale bar (115) is displayed.

Figure 13:
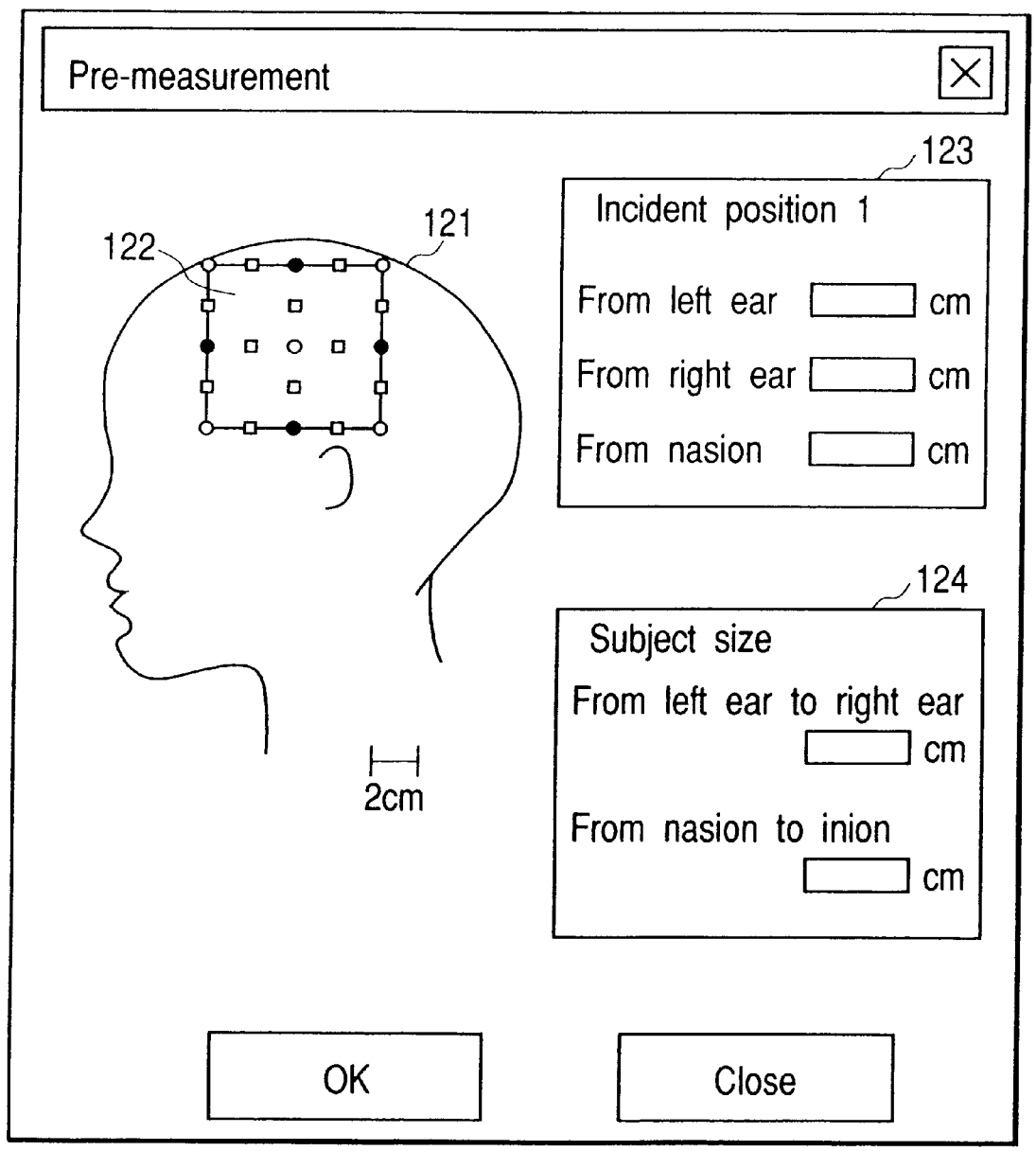
FIG. 13 is a diagram showing a window in which an arrangement of measurement positions is overlapped with an outer shape of a test object in the embodiment.

In order to clearly display the positional relationship among the incident positions and the detection positions and the measurement positions, a group of the graphic elements 122, such as the incident positions and the detection positions and the measurement positions, may be superposed on an image or a line picture (121) representing the shape of the test object, as shown in FIG. 13. Further, in order to specify each of the incident and the detecting positions in the test object, numerical values expressing coordinates on the test object of the positions of the incident and the detecting positions are input (123). By defining the numerical values by distances along the head from the right ear, from the left ear and from a position anatomically called as nasion (the boundary between the forehead and the nose), the coordinates on the head can be uniquely and simply expressed as specific values. Further, in order to show the size of the test object on this occasion, a linear distance and a distance on the head between the right ear and the left ear, and a linear distance and a distance on the head between the nasion and the inion (an anatomical position existing on the median in the occipital) are also input (124).

Figure 14:
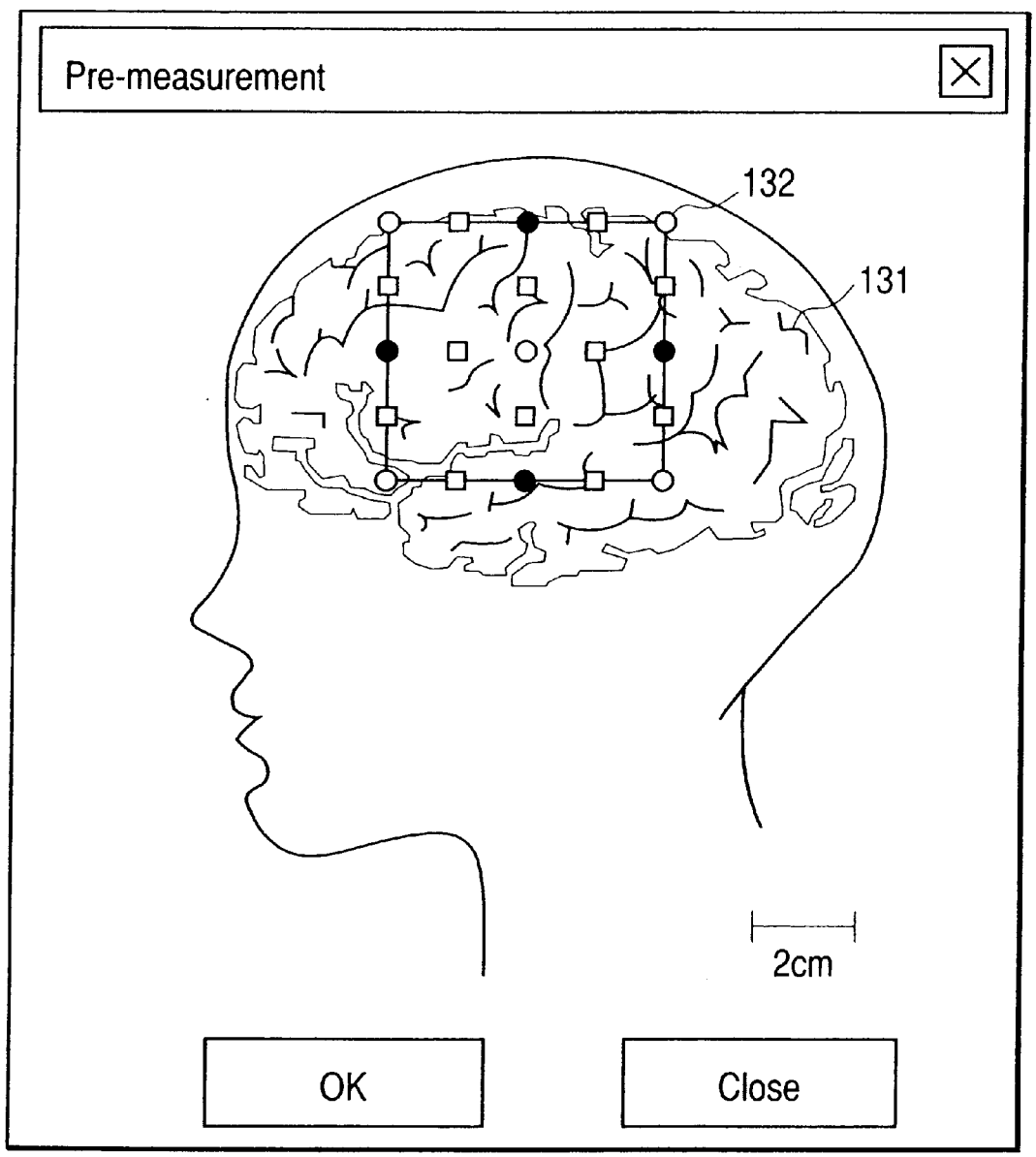
FIG. 14 is a diagram showing a window in the embodiment in which an arrangement of measurement positions is overlapped with an outer shape of a test object.
Figure 15:
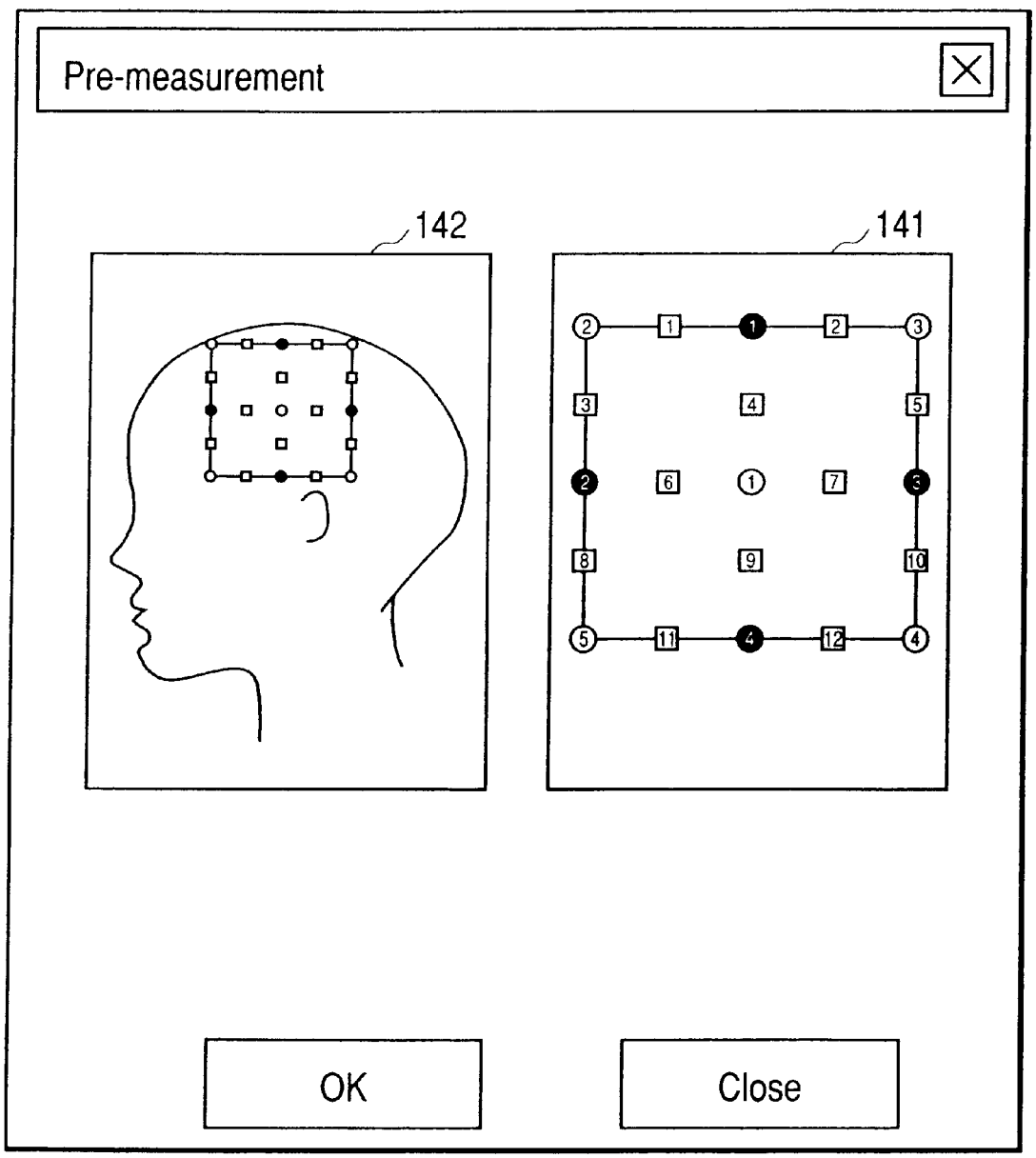
FIG. 15 is a diagram showing a display in the embodiment in which the window showing an arrangement of measurement positions is overlapped with an outer shape of a test object and the structure of a basic window are displayed side by side.

In addition to the image showing the outer shape of the test object, an inner shape, for example, an image showing the anatomical structure of the cerebrum may be used. For example, as shown in FIG. 14, a group of the graphic elements 132, such as the incident positions and the detection positions, may be superposed on an inner shape image (131), such as an MRI image, a CT image, an ultrasonic wave image or the like. There, as shown in FIG. 15, a display of only the graphic elements as shown in FIG. 1 and a display superposing an outer shape and the graphic elements as shown in FIG. 13 may be shown on a single display screen side by side.

For example, on the window of FIG. 1 displayed on the display unit 20, when the graphic element corresponding to the incident optical fiber 8-1 (the incident position 1) is selected using the operation unit (for example, the corresponding graphic element is clicked), the background of the corresponding graphic element is changed from black, for example, to pink, and the display element 32 mounted to the support portion 31 of the top end of the incident optical fiber number 8-1 shown in FIG. 7 lights up to show that the optical fiber is the optical fiber to be mounted corresponding to the graphic element selected just before. In that case, the pink color means that the graphic element is in a state of being mounted. Further, by selecting the graphic element of the incident optical fiber 8-1 on the widow of FIG. 1, the display element in the optical fiber holder 52 arranged in the probe 21 also lights up in the corresponding optical fiber holder to show both the optical fiber to be mounted and the position where the optical fiber is to be mounted in the probe. Thereby, an operator can speedily and efficiently mount the corresponding optical fiber to the appropriate position without mistake. After completion of mounting the optical fiber, for example, the graphic element of the detection optical fiber 10-1 (the detection position 1) is selected next on the window of FIG. 1. Then, the background in the graphic element expressing the incident optical fiber 8-1 is changed, for example, from pink to sky blue. The sky blue color indicates a state of completion of mounting. Then, the background in the graphic element expressing the detection optical fiber 10-1 is changed to pink, and the display element of the top end of the corresponding detection optical fiber 10-1 lights up, and the display element of the corresponding optical fiber holder 52 in the probe 21 lights up. Of course, the change in each of graphic elements described here is not limited to the change in the colors described above, but any colors may be used so long as they can be identified. Further, in each of the graphic elements, the change in the mounting states may be displayed by change of patterns such as hatching, crosshatching and the like, in addition to the change in colors. After mounting the other optical fibers in a similar way and completing the mounting of all the optical fibers, the OK button (116) on the display window of FIG. 1 is selected. If the Close button (117) is selected, the display is returned to the preceding window, in this case, it is returned to the measurement arrangement mode selection window.

Figure 16:
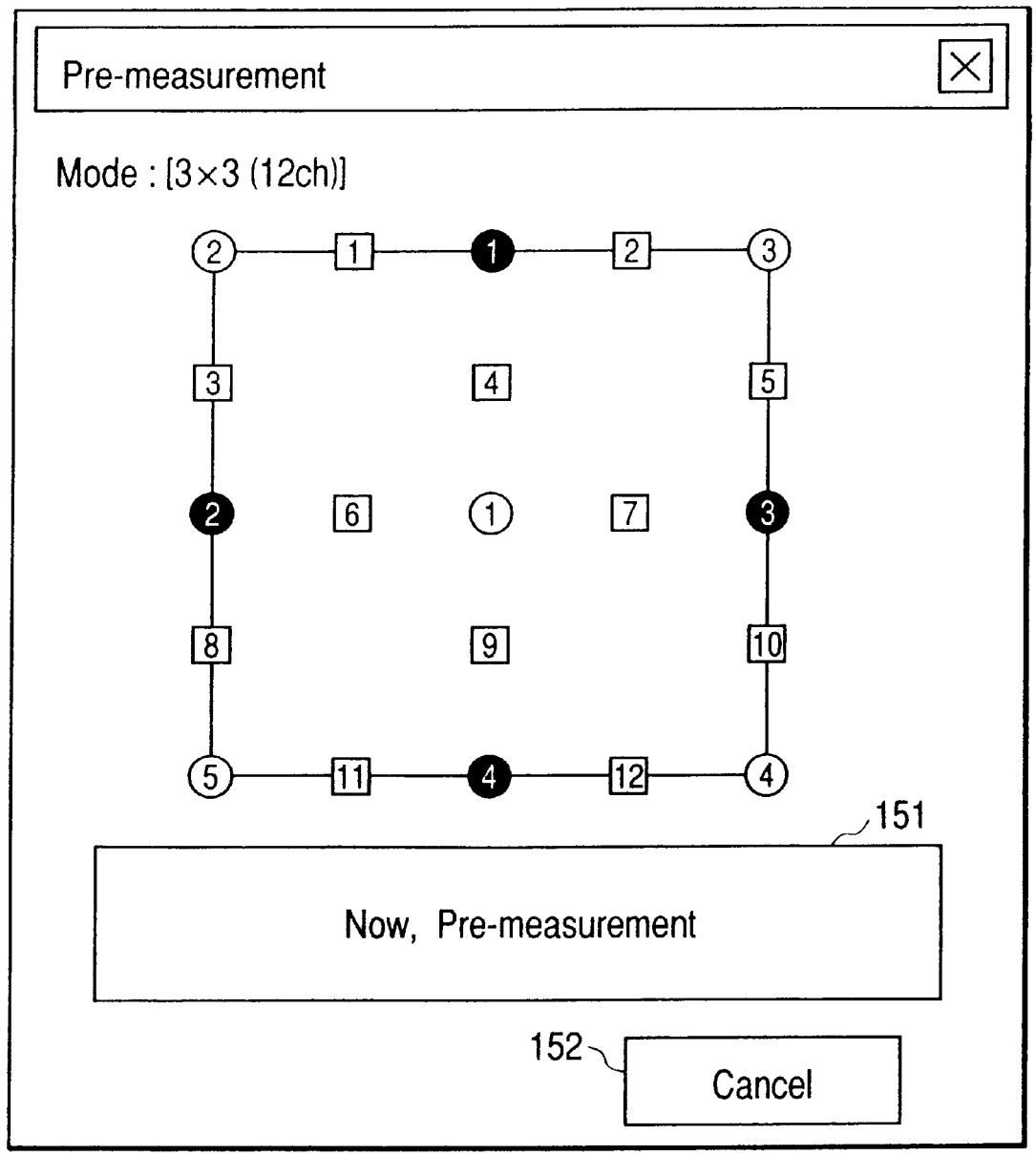
FIG. 16 is a diagram showing an example of a window for displaying pre-measurement in progress in the embodiment.

By selection of the OK button (116), the background of each of the graphic elements is returned to the original color, and the preparation measurement described below is executed. During execution of the preparation measurement, the status indicator preparation measurement in progress (151) as shown in FIG. 16 is displayed on the display screen. The preparation measurement can be canceled by way of the Cancel button (152). The preparation measurement is performed prior to actual measurement of the change in concentrations, such as hemoglobin, that is, prior to regular measurement.

Figure 17:
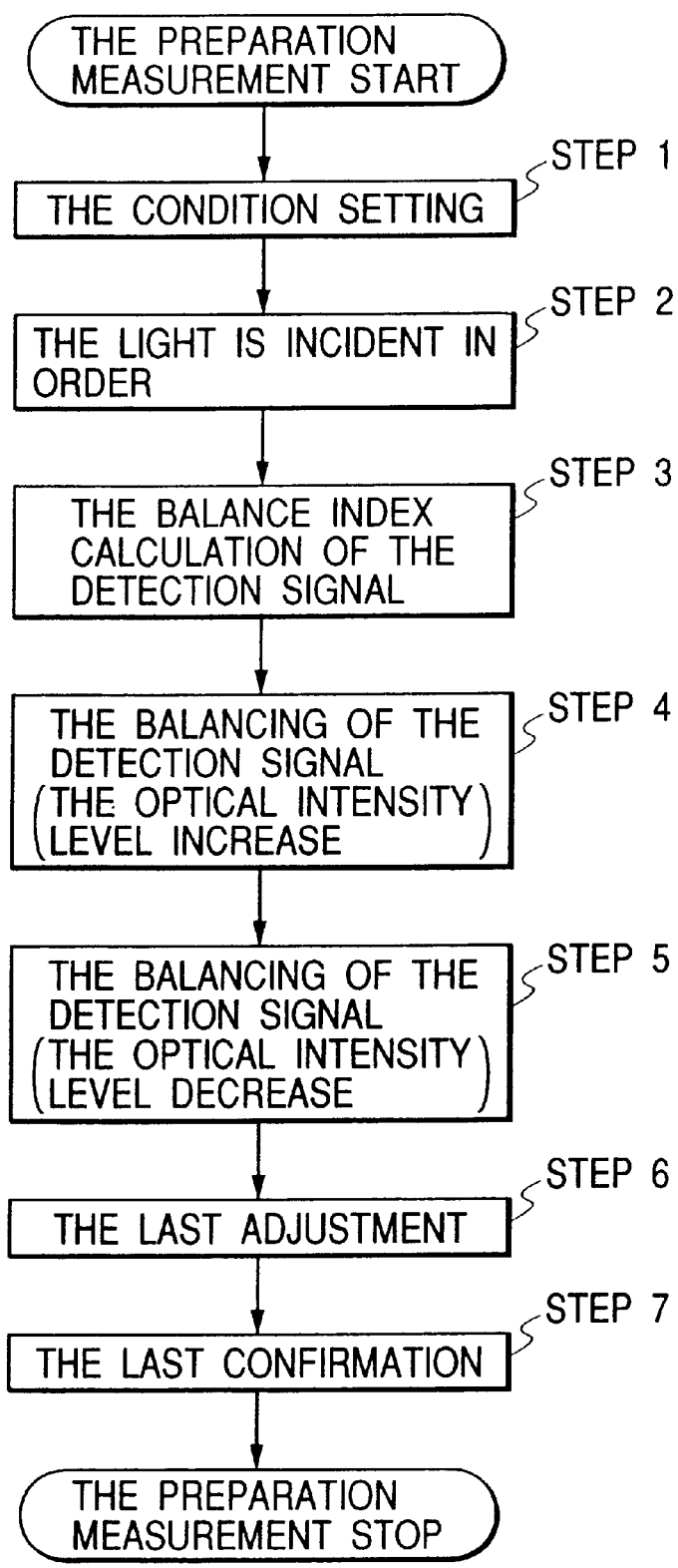
FIG. 17 is a flowchart showing the outline of the overall of the pre-measurement in the embodiment.
Figure 18:
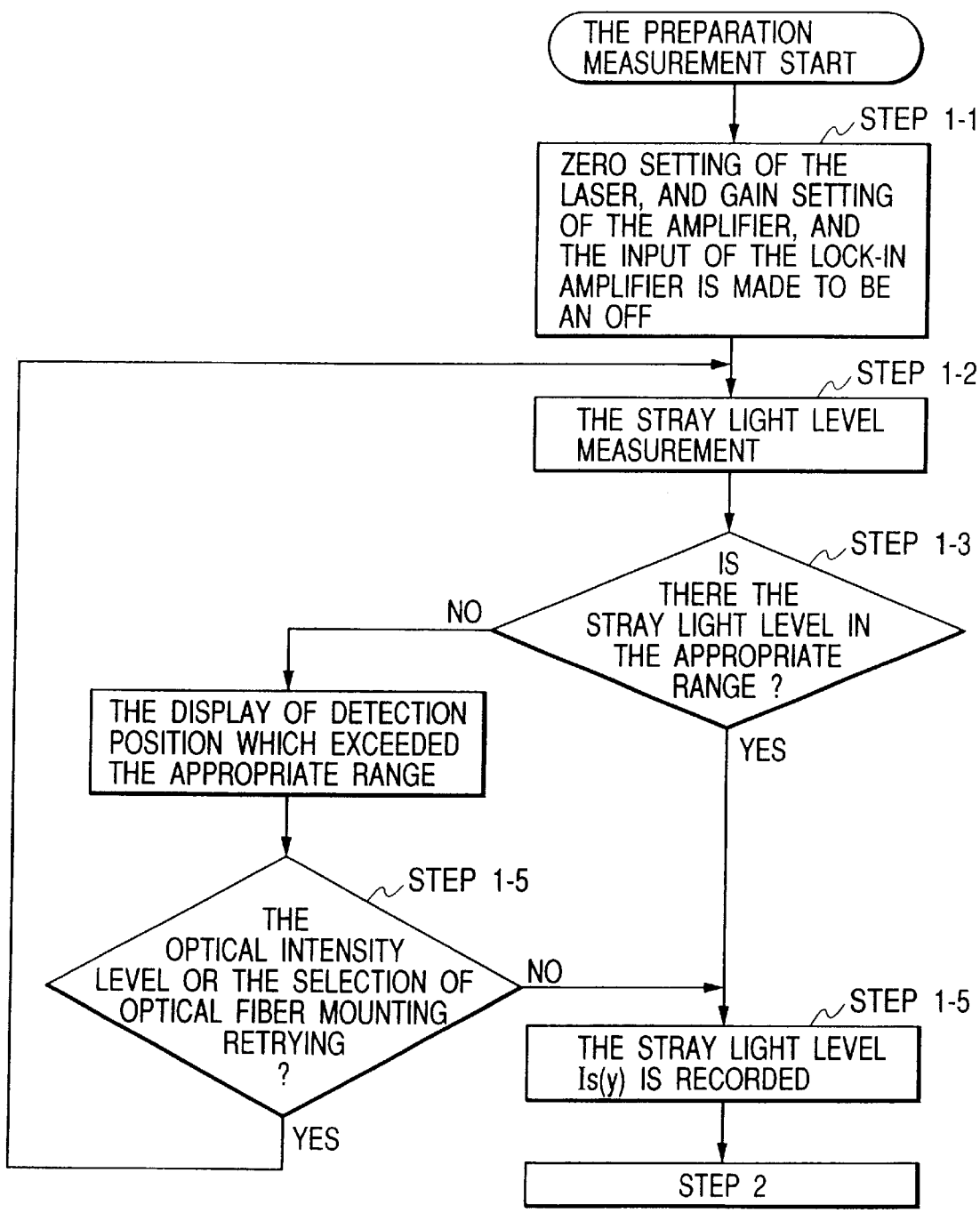
FIG. 18 is a flowchart showing the details of the condition setting processing in the step 1 of the pre-measurement in the embodiment.
Figure 19:
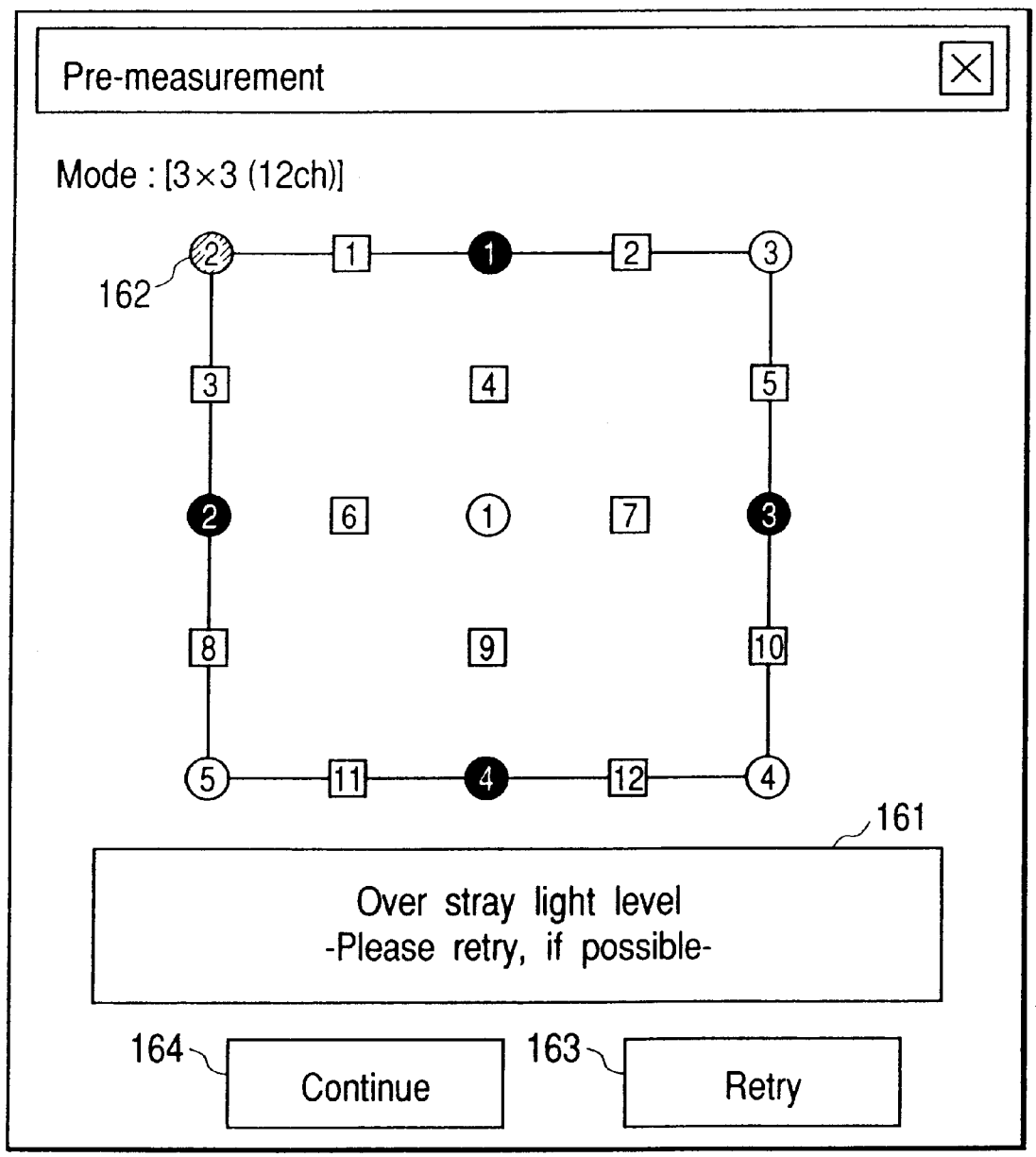
FIG. 19 is a diagram showing a window displaying a high stray light level during the pre-measurement in the embodiment.

FIG. 17 is a flowchart showing the outline of the overall preparation measurement. Each Process Step in FIG. 17 will be described in detail below.
(Step 1: Condition Setting)
The details of the condition setting process will be described with reference to the flowchart shown in FIG. 18.
(Step 1-1)
By controlling the drive circuit 4 of the light source 1 using the control unit 17, the optical intensities of all of the laser diodes are set to zero level, and the gains of the amplifiers 14 in the lock-in amplifier modules 12 are set to a set value, for example, to 1. Further, each of the switches 15 connected to the output of an amplifier is turned off, so that the signal from each amplifier may be not input to its corresponding lock-in amplifier, but may be directly input to the analogue-to-digital converter 16.
(Step 1-2)
Under the condition that the optical intensities from all the laser diodes are zero, an direct current output from each of the photodiodes is measured as a stray light level.
(Step 1-3)
When a stray light level exceeds an appropriate range, a detection position corresponding to the photodiode is displayed on the display unit 20. An example of the display is shown in FIG. 19. It is displayed in letters on the display screen that the stray light level exceeds the appropriate range (161), and in the measurement position arrangement figure, the background of the graphic element representing the detection position corresponding to the portion exceeding the appropriate stray light level is also displayed in yellow. For example, FIG. 19 shows an example shown by hatching instead of the yellow background for the sake of convenience as a case where the stray light level exceeds the appropriate stray light level at the "detection position 2" (162).
(Step 1-4)
Reconsideration of the optical intensity level in the measurement room or of the state of mounting the optical fiber is recommended to the operator, as shown in FIG. 19, and the processing is returned to Step 1-2 if the operator selects the Retry button (163) on the screen in FIG. 19. If the Retry operation is not selected and the Continue button is selected, the processing proceeds to Step 1-5.
(Step 1-5)
The stray light level value Is(y) corresponding to each of the photodiodes 11-y is recorded in the recording unit 18, where y is a variable indicating the detection positions.

Figure 20:
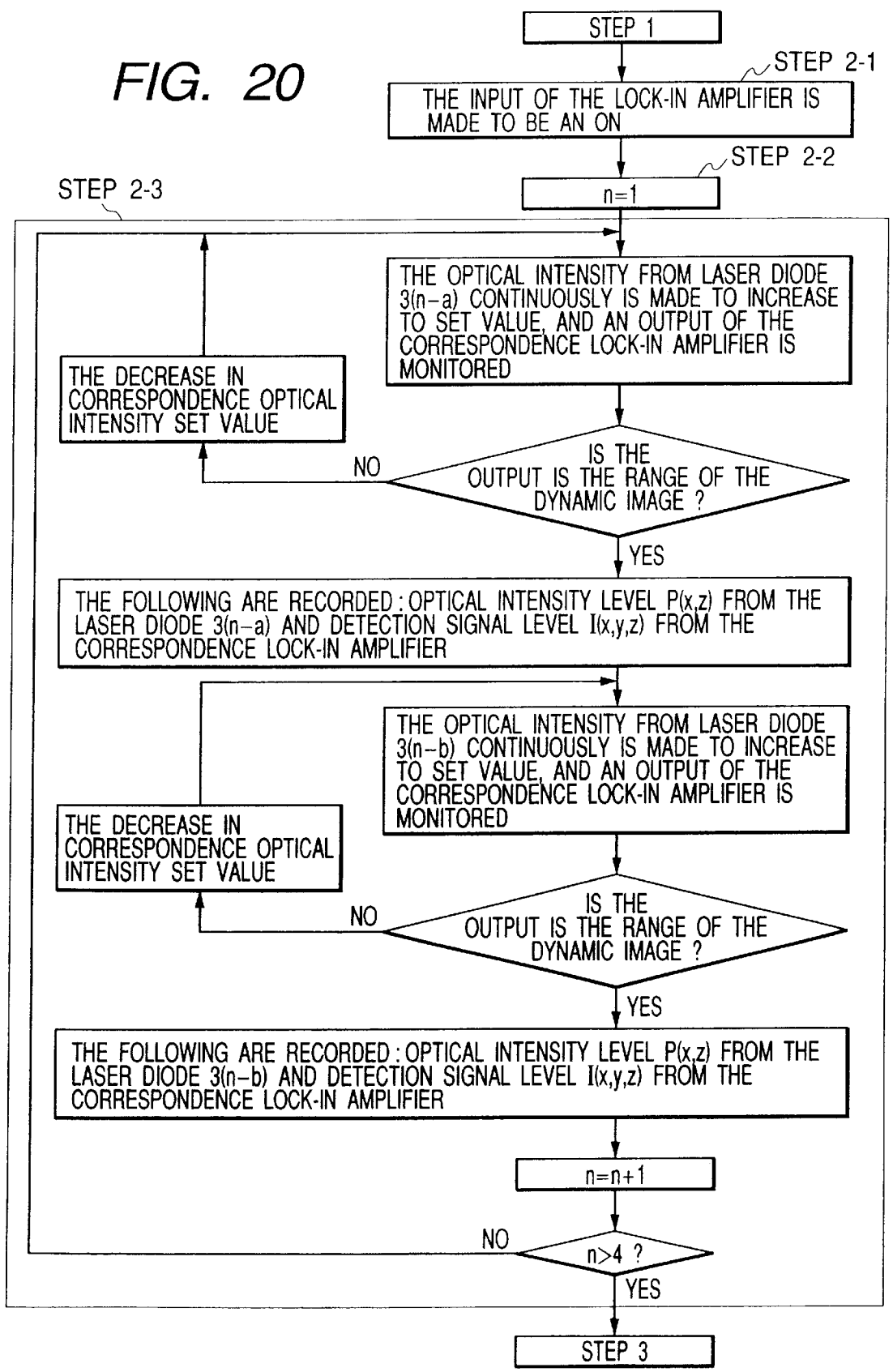
FIG. 20 is a flowchart showing the details of the light incident in-order processing in the step 2 of the pre-measurement in the embodiment.

(Step 2: Light is Incident in Order)
The details of the process of determining that the light is incident in order will be described with reference to the flowchart shown in FIG. 20.
(Step 2-1)
Each of the switches 15 in the lock-in amplifier module 12 is turned on so that the output signal from the amplifier 14 may be input to each of the lock-in amplifiers.
(Step 2-2)
A numerical value of 1 is substituted into a variable n.
(Step 2-3)
In the case of the incident position n, here, in the case of n=1, by controlling the drive circuit 4 (1-a) and the oscillator 3 relating to the laser diode 3 (1-a) of wavelength 780 nm which illuminates the "incident position 1", the optical intensity from the laser diode is continuously or discretely increased from zero level up to a set value. Therein, at the same time, the detection signals are measured in the lock-in amplifiers which are connected to the photodiodes 11-1 to 11-3 corresponding to the "detection positions 1, 2, 3" adjacent to the "incident position 1" and which are in synchronism with the same frequency as the modulation frequency f(1-a) of the laser diode 3 (1-a). At that time, it is checked to determine that the response of the detection signal level of each of the lock-in amplifiers to the change of optical intensity level of the light source is within a range of linear response of all of the photodiodes and all of the lock-in amplifiers, that is, within the dynamic range. If any one of the detection signal levels exceeds the dynamic range and loses its linearity, the set value of the optical intensity from the laser diode 3 (1-a) is decreased to an appropriate level, and the same operation is repeated.

At that time, both the optical intensity level of the laser diode and the detection signal level from each of the lock-in amplifiers are recorded. For example, the variable expressing the incident position is designated x, the variable expressing the detection position is designated y, the character variable expressing the wavelength is designated z, the optical intensity level is designated P(x, z), and the detection signal level is designated I(x, y, z). The designation z is replaced by the letter a when the wavelength is 780 nm, and by the letter b when the wavelength is 830 nm.

After that, the optical intensity of the laser diode is set to zero.

Next, in the case of the incident position n, here, in the case of n=1, in regard to the laser diode 3 (1-b) of wavelength 830 nm illuminated to the "incident position 1", the same operation as used in the case of the wavelength 780 nm described above is performed.

Figure 21:
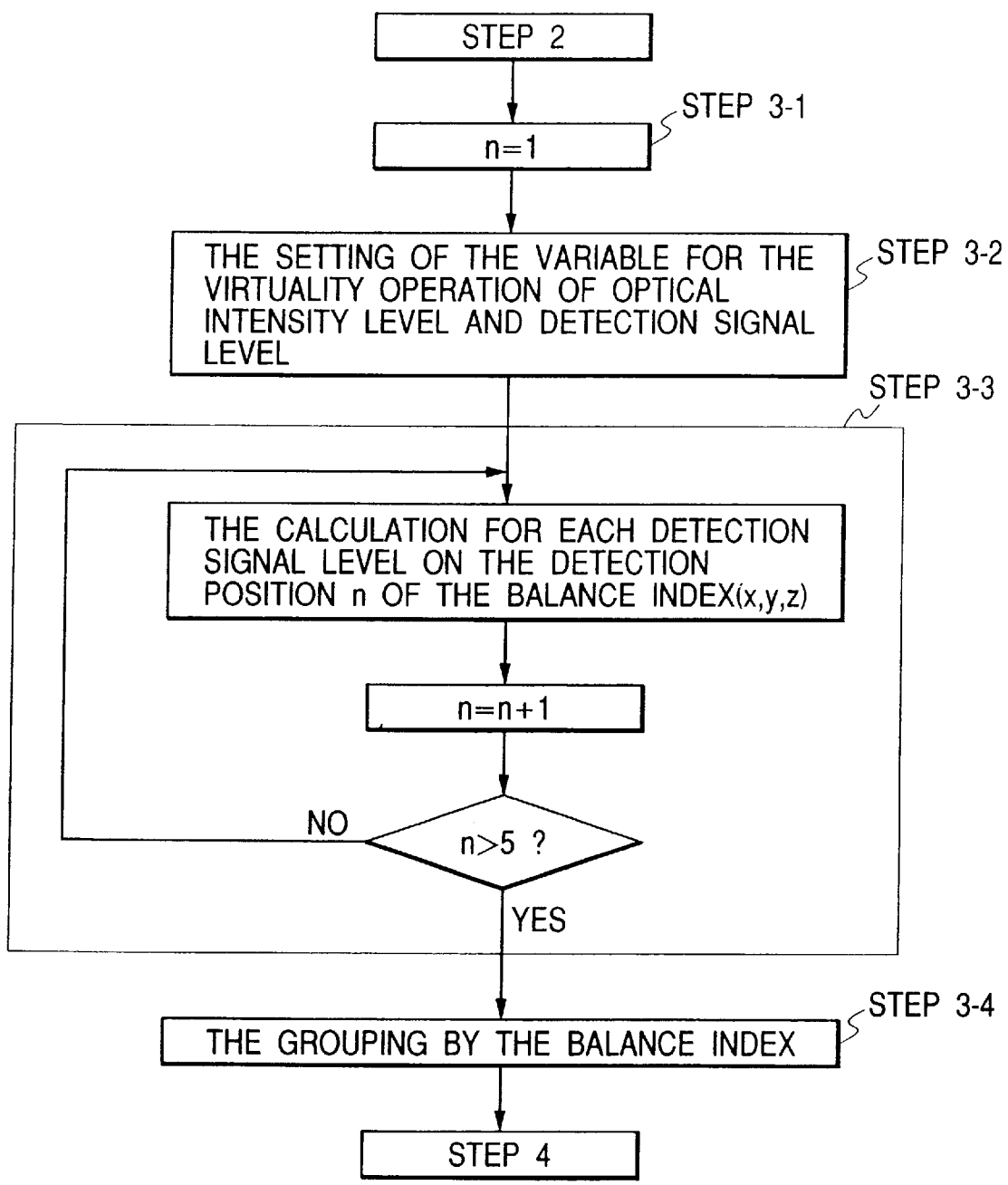
FIG. 21 is a flowchart showing the details of the detection signal balance index calculation processing in the step 3 of the pre-measurement in the embodiment.

Next, n is increased by 1. If n is smaller than or equal to the number of the incident positions, that is, if n is smaller than or equal to 4, the same operation is repeated for the laser diodes 3 (n-a) and 3 (n-b).
(Step 3: Balance Index Calculation of the Detection Signal)
The detail of the process of the balance index calculation of the detection signal will be described with reference to the flowchart shown in FIG. 21.
(Step 3-1)
A numerical value of 1 is substituted into the variable n.
(Step 3-2)
The optical intensity level P(x,z) and the detection signal level I(x, y, z) introduced in Step 2-3 are used as the initial condition, and variables of the virtuality operation Pv(x,z) and Iv(x, y,z) are set.
(Step 3-3)
An average value of detection signal levels other than the stray light level detected by the photodiodes 11-n corresponding to the detection position n is designated Im(n). That is, for example, in the case of n=1, an average value of detection signal levels except for the stray light level Iv(1, 1, a), Iv(1, 1, b), Iv(2, 1, a), Iv(2, 1, b), Iv(3, 1, a), Iv(3, 1, b), Iv(4, 1, a), Iv(4, 1, b) detected by the photodiodes 11-1 is designated Im(1). A ratio of each detection signal level to the average value is calculated as a balance index. The balance index is expressed by V(x, y, z) using three variables, including the incident position x, the detection position y and the wavelength z. For example, the balance index V(1, 1. a) to the detection signal level Iv(1, 1. a) is Iv(1, 1. a)/Im(1).

The meaning of the index is that when the value of V(x, y, z) is 1, the corresponding signal level is average, and when the value of V(x, y, z) is larger than 1, the corresponding signal level is strong, and when the value of V(x, y, z) is smaller than 1, the corresponding signal level is weak. When all the indexes in all the signals from the identical photodiode, it means that the detection signal level is in balance. When indexes largely exceeding 1 and near zero exist, it means that the detection signal level is in strong unbalance.

Figure 22:
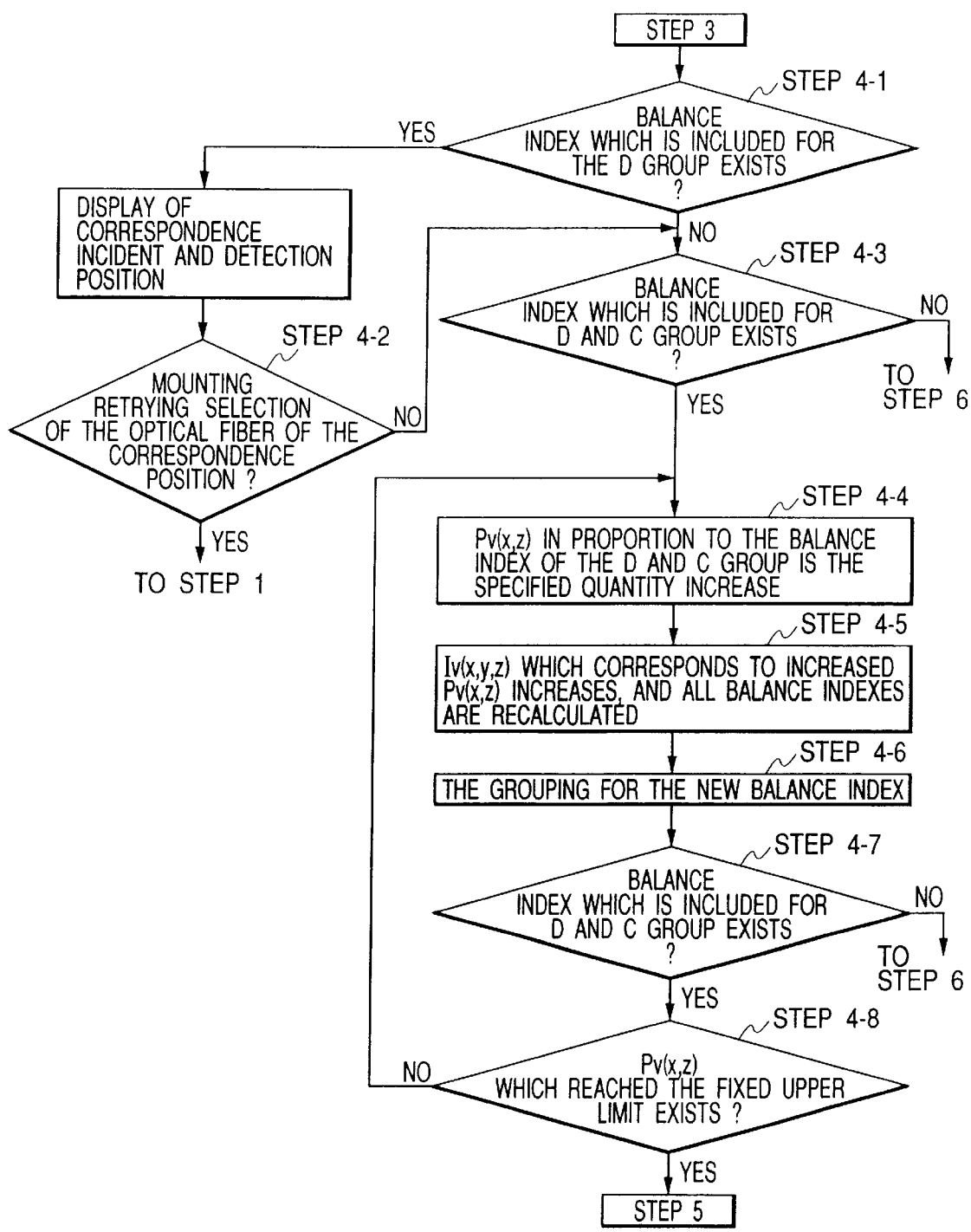
FIG. 22 is a flowchart showing the details of the detection signal balancing (optical intensity level increase) processing in the step 4 of the pre-measurement in the embodiment.
Figure 23:
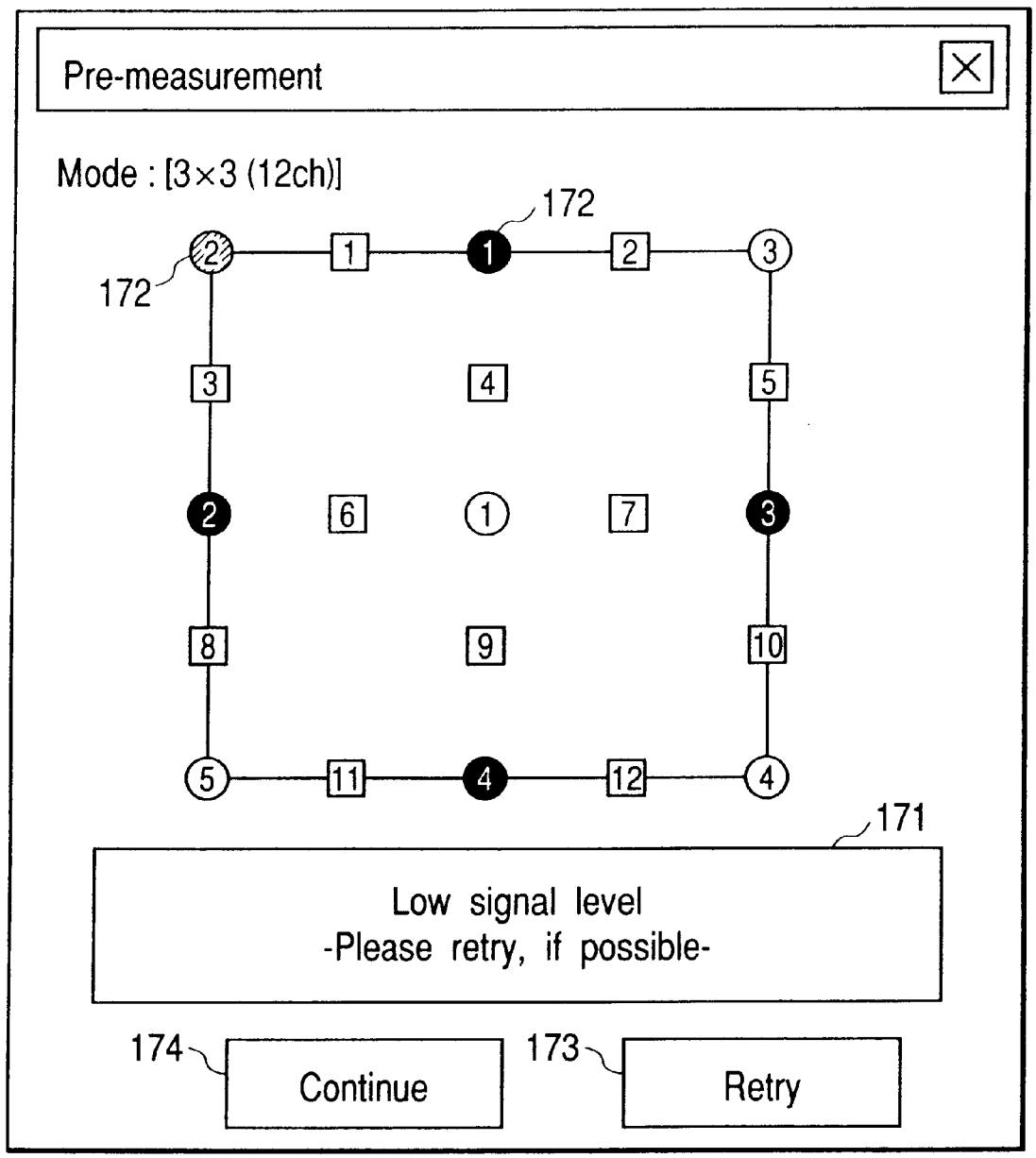
FIG. 23 is a diagram showing a window displaying a low signal level during the pre-measurement in the embodiment.

Next, n is increased by 1. If n is smaller than or equal to the number of the detection positions, that is, if n is smaller than or equal to 5, the same operation is repeated for the laser diodes 11-n for the detection position n, and the balance indexes are calculated for all detection signal levels.
(Step 3-4)
All the balance indexes V(x, y, z) calculated in Step 3-3 are grouped according to the values. For example, the balance indexes V(x, y, z) larger than 1.5 belong to an A group, the balance indexes V(x, y, z) from 1.5 to 0.5 belong to a B group, the balance indexes V(x, y, z) from 0.5 to 0.2 belong to a C group, and the balance indexes V(x, y, z) smaller than 0.2 belong to a D group. The unbalance of the detection signals often occurs in a specific incident position or a specific detection position, such as a condition of a measurement position or optical fiber mounting. Therefore, the C and D groups include many balance indexes relating to a common optical fiber. Such incident positions and such detection positions are obtained, and the incident positions and the detection positions belonging to the A group are extracted.
(Step 4: Balancing of the Detection Signals (Optical Intensity Level Increase))
The details of the process of balancing the detection signals (optical intensity level increase) will be described with reference to the flowchart shown in FIG. 22.
(Step 4-1)
If there is any balance index V(x, y, z) classified to the D group in the grouping of the balance indexes, the corresponding incident positions and the corresponding detection positions or the corresponding measurement positions are displayed on the display unit 20. An example of the display is shown in FIG. 23. On the displayed picture, it is indicated by letters that the detection signal level is lower than the appropriate range (171), and in the optical fiber position arrangement figure, the background of the graphic element representing the corresponding incident position and the corresponding detection position are displayed in yellow in the case of the D group. For example, FIG. 23 shows an example using hatching instead of the yellow background color for the sake of convenience as a case where the detection signal level relating to the "detection position 2" and the incident position 1 is lower than the appropriate level (172).

Figure 24:
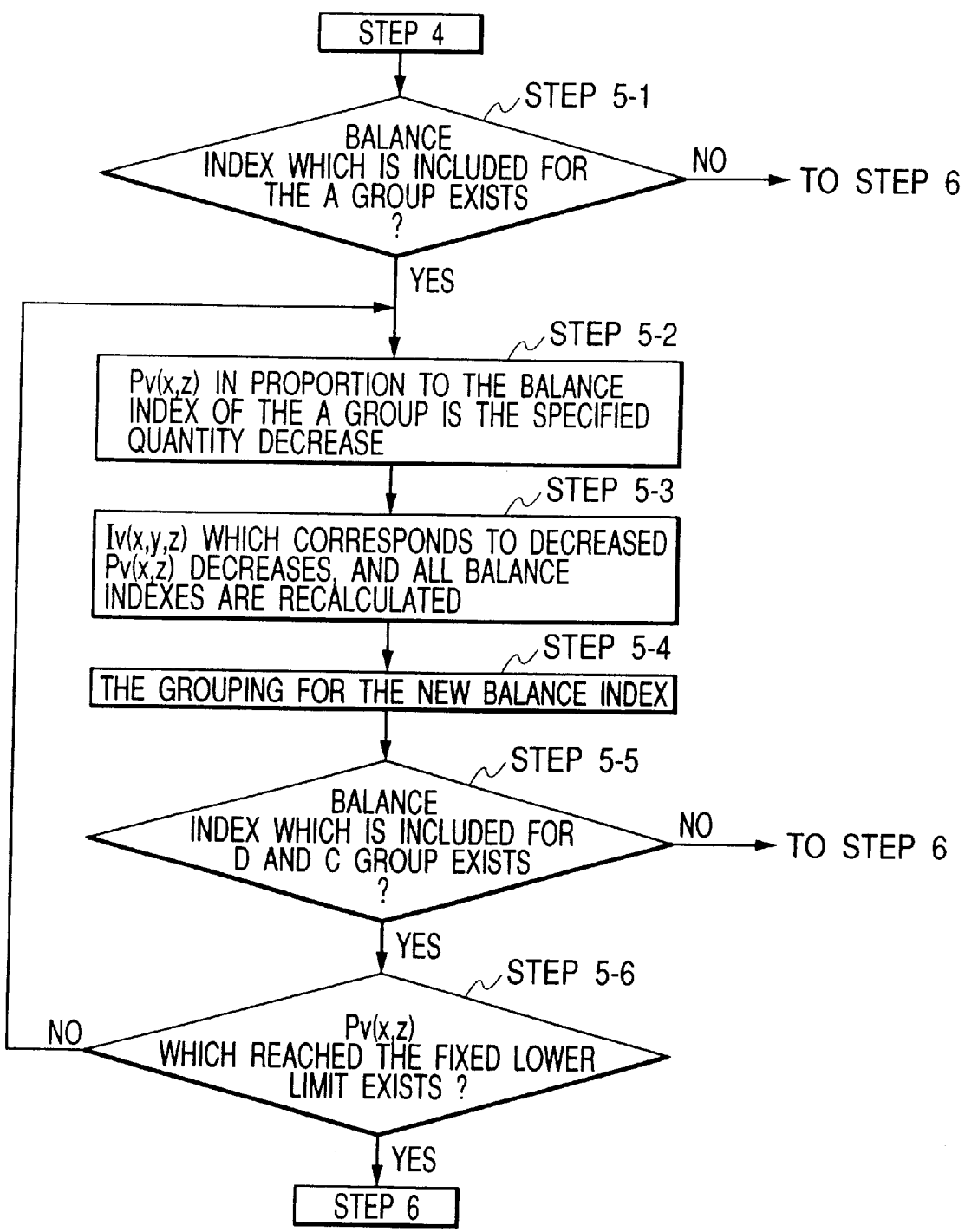
FIG. 24 is a flowchart showing the details of the detection signal balancing (optical intensity level decrease) processing in the step 5 of the pre-measurement in the embodiment.
Figure 25:
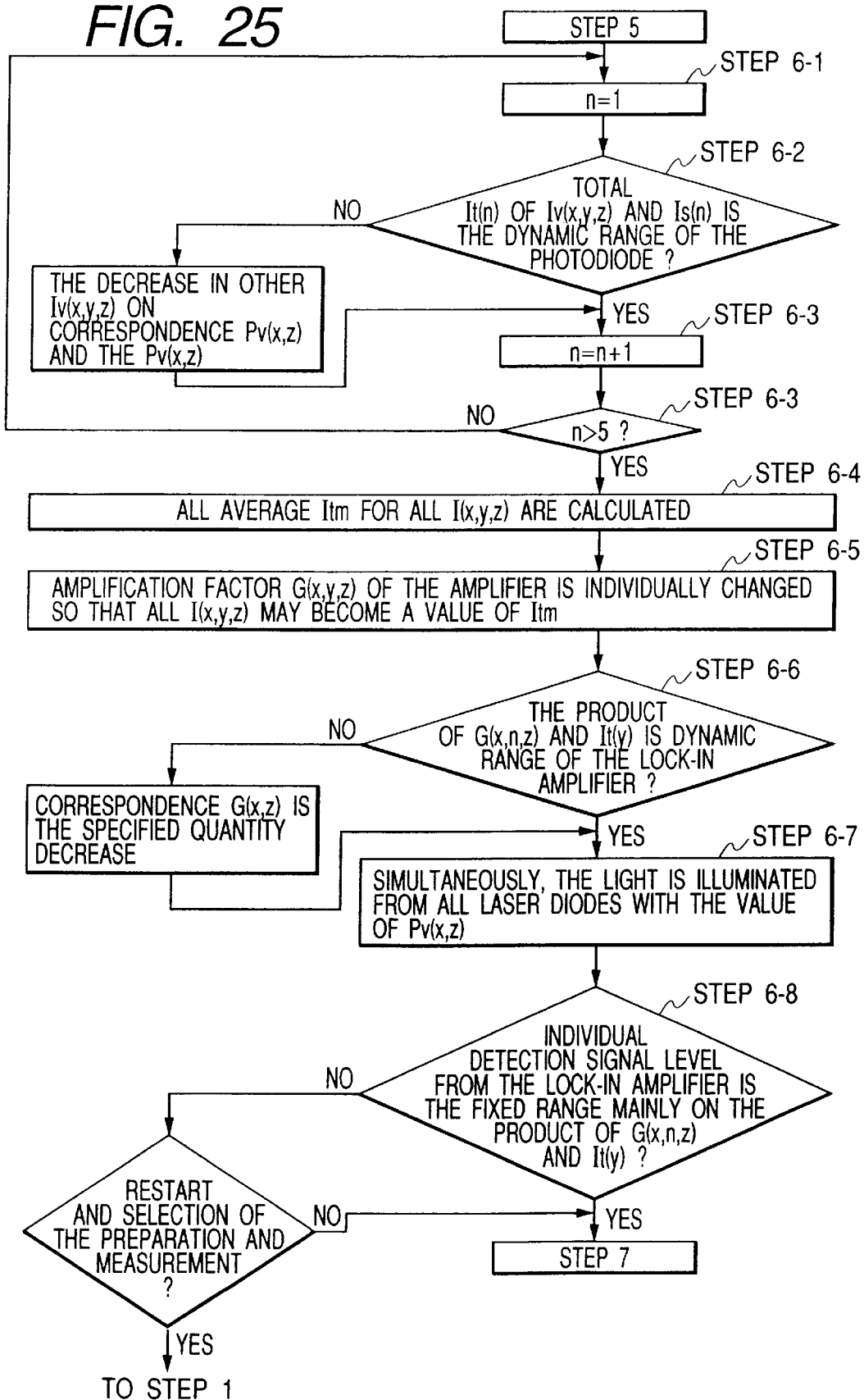
FIG. 25 is a flowchart showing the details of the last adjustment processing in the step 6 of the pre-measurement in the embodiment.
Figure 26:
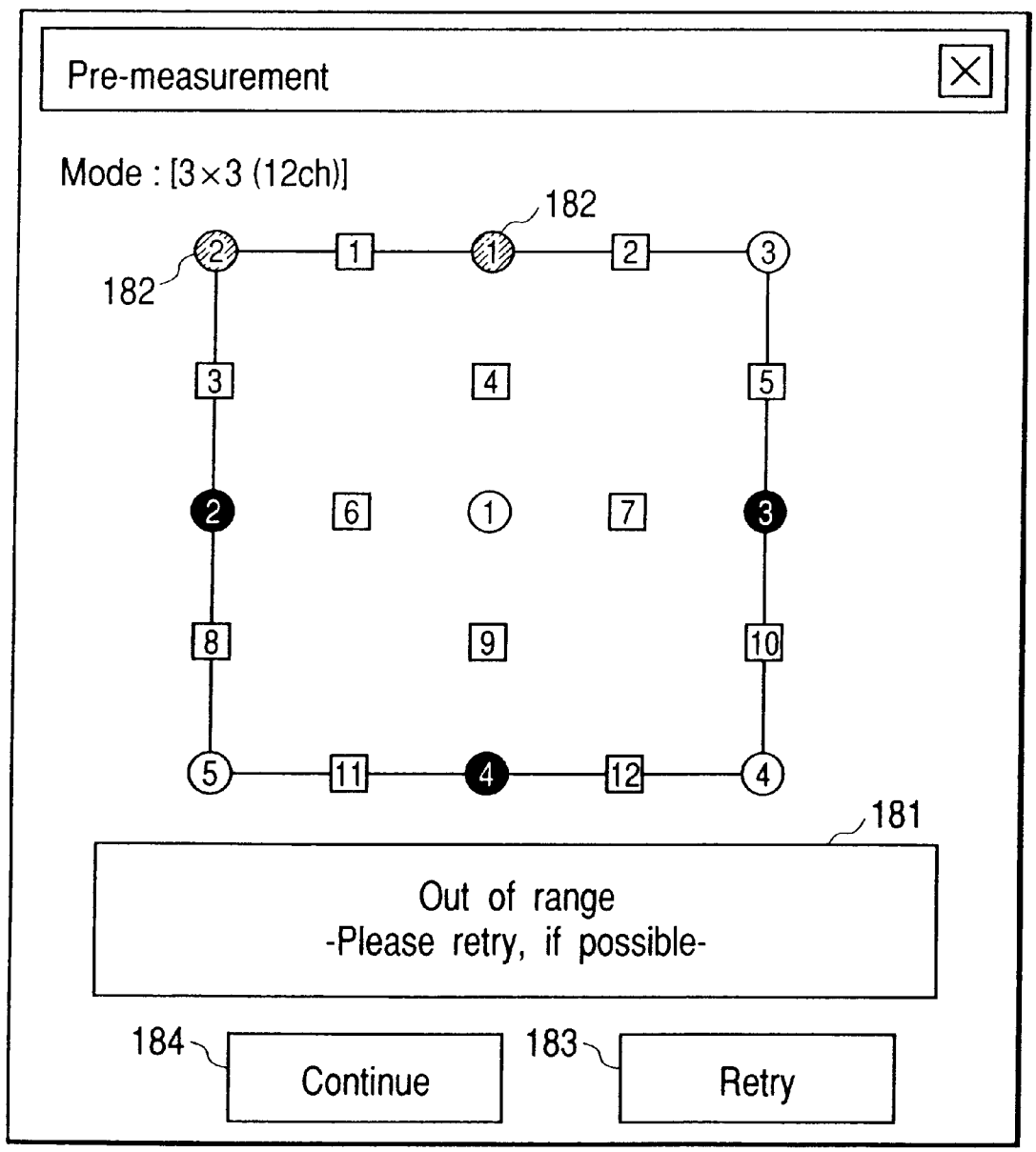
FIG. 26 is a diagram showing a window for displaying a range over during the pre-measurement in the embodiment.

Further, such display may be shown by a background color of the graphic element representing the measurement position uniquely obtained by the corresponding incident position and the corresponding detection position.
(Step 4-2)
Retrying of re-mounting the optical fibers in the corresponding incident position and the corresponding detection position is recommended to the operator as shown in FIG. 23, and the processing is returned to Step 1 if the operator selects the Retry button (174). If the Continue button is selected, the processing proceeds to Step 4-3.
(Step 4-3)
If there is no balance index V(x, y, z) classified to the D and C groups in the grouping of the balance indexes, the processing proceeds to Step 6.
(Step 4-4)
The virtuality operation of optical intensity level Pv(x, z) from the incident position corresponding to the balance indexes of the D and C groups is increased by a specified increment, and the value of Pv(x, z) is replaced by the increased value.
(Step 4-5)
To all the virtuality operation detection signal levels Iv(x, y, z) corresponding to the incident position of the optical intensity level Pv(x, z) increased in Step 4-4, the values of Pv(x, z) are replaced by values in proportion to the increased ratio of Pv(x, z), respectively, and all of the values of V(x, y, z) are also replaced by new values by performing a recalculation.
(Step 4-6)
For the new balance indexes, grouping is executed again.
(Step 4-7)
If there is no balance index V(x, y, z) classified to the D and C groups, the processing proceeds to Step 6.
(Step 4-8)
If there is a level of Pv(x, z) which reaches the fixed upper limit, the processing proceeds to Step 5. If there is no level of Pv(x, z) which reaches the fixed upper limit, the processing is returned to Step 4-4 to repeat the same operation.
(Step 5: Balancing of the Detection Signal (Optical Intensity Level Decrease))
The details of the process of balancing the detection signals (optical intensity level decrease) will be described with reference to the flowchart shown in FIG. 24.
(Step 5-1)
If there is no balance index V(x, y, z) classified to the A group in the grouping of the balance indexes, the processing proceeds to Step 6.
(Step 5-2)
The virtuality operation of optical intensity level Pv(x, z) from the incident position corresponding to the balance indexes of the A group is decreased by a specified decrement, and the value of Pv(x, z) is replaced by the decreased value.
(Step 5-3)
To all the virtuality operation detection signal levels Iv(x, y, z) corresponding to the incident position of the optical intensity level Pv(x, z) increased in Step 5-2, the values of Pv(x, z) are replaced by values in proportion to the decreased ratio of Pv(x, z), respectively, and all of the values of V(x, y, z) are also replaced by new values by performing a recalculation.
(Step 5-4)
For the new balance indexes, grouping is executed again.
(Step 5-5)
If there is no balance index V(x, y, z) classified to the D and C groups, the processing proceeds to Step 6.
(Step 5-6)
If there is a level of Pv(x, z) which reaches the fixed lower limit, the processing proceeds to Step 6. If there is no level of Pv(x, z) which reaches the fixed lower limit, the processing is returned to Step 5-1 to repeat the same operation.
(Step 6: Last Adjustment)
The details of the process of the last adjustment will be described with reference to the flowchart shown in FIG. 25.
(Step 6-1)
The numerical value 1 is substituted to the variable n.
(Step 6-2)
A total sum of the value of the stray light level Is(n) and the detection signal levels Iv(x, n, z) detected by the photodiodes 11-n corresponding to the detection position n is designated It(n). That is, for example, in the case of n=1, a total sum of the value of the stray light level Is(1) and the detection signal levels Iv(1, 1, a), Iv(1, 1, b), Iv(2, 1, a), Iv(2, 1, b), Iv(3, 1, a), Iv(3, 1, b), Iv(4, 1, a), Iv(4, 1, b) detected by the photodiodes 11-1 is designated Im(1). If the value of the total sum exceeds the dynamic range of the photodiode, the corresponding detection signal levels Iv(x, y, z) are reduced by a uniform ratio so that It(n) may become the fixed upper limit, and Pv(x, z) relating to the reduced Iv(x, y, z) and Iv(x, y, z) relating to Pv(x, z) are also reduced by the same ratio.
(Step 6-3)
Next, n is increased by 1. If n is smaller than or equal to the number of the detection positions, that is, if n is smaller than or equal to 5, the same operation is repeated for the detection position n.
(Step 6-4)
All average values of Itm for all the virtuality operation variables Iv(x, y, z) are calculated.
(Step 6-5)
Amplification factor G(x, y, z) of each of the amplifiers 14 in the lock-in amplifier module 12 is independently changed so that the detection signal level of all values of Iv(x, y, z) may become the value Itm. Therein, the amplification factor of the amplifiers relating to each of the values of Iv(x, y, z) is designated G(x, y, z).
(Step 6-6)
If the product of It(y) and G(x, y, z) input to each of the lock-in amplifiers exceeds the dynamic range of the lock-in amplifier, G(x, y, z) relating to the corresponding lock-in amplifier is reduced so that the product of It(y) and G(x, y, z) may become the fixed upper limit of the dynamic range.
(Step 6-7)
According to the value of Pv(x, z) in each of the incident positions and in each of the wavelengths at the time point of this step, light is actually simultaneously illuminated from all the laser diodes in the light source 1.
(Step 6-8)
If each of the actual detection signal levels from each of the lock-in amplifiers is out of the fixed range mainly on the product of Iv(x, y, z) and G(x, y, z), the operator is informed of the fact by way of the display. FIG. 26 shows an example of such a display. On the displayed picture, it is indicated by letters that the detection signal level is out of the appropriate range (181), and in the optical fiber position arrangement figure, the background color of the graphic element representing the corresponding incident position and the corresponding detection position is displayed in yellow. For example, FIG. 26 shows an example where hatching is used instead of the yellow background color for the sake of convenience as a case where the detection signal level relating to the detection position 2 and the incident position 1 is low and out of the appropriate level (182).

Further, such display may be shown by a background color of the graphic element expressing the measurement position uniquely obtained by the corresponding incident position and the corresponding detection position. If the operator selects the Retry button (183) for the preparation measurement, the processing is returned to Step 1. If the Continue button (184) is selected, the processing proceeds to Step 7.

(Step 7: Last Confirmation)

Figure 27:
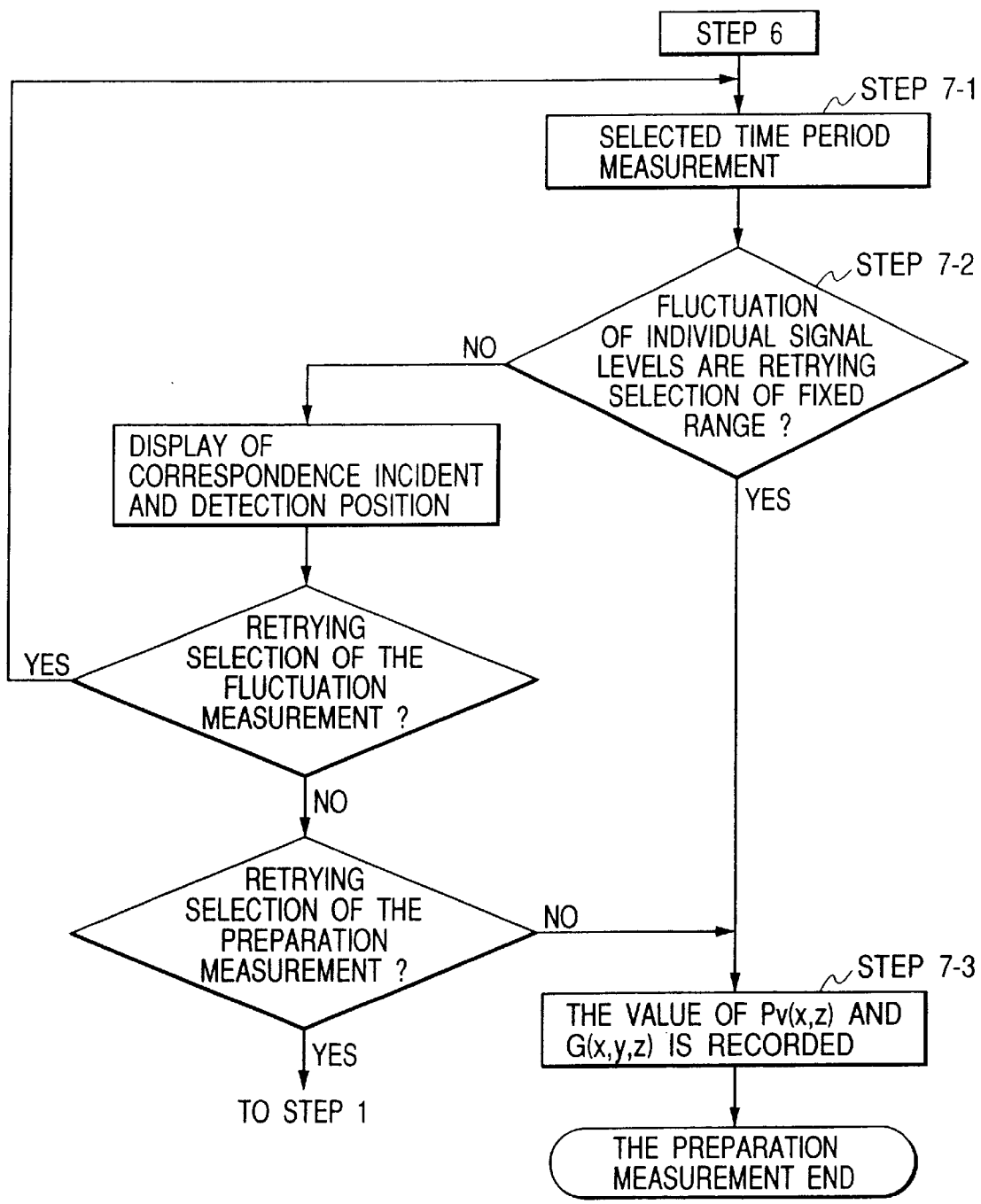
FIG. 27 is a flowchart showing the details of the last confirmation processing in the step 7 of the pre-measurement in the embodiment.

The details of the process of the last confirmation will be described with reference to the flowchart shown in FIG. 27.

(Step 7-1)

By keeping the condition of the light illumination and the light detection in Step 6-8 for a selected time period, for example, 30 seconds, measurement is performed. Of course, the time period is not limited to 30 seconds.

During that time period, all the detection signal levels I(x, y, z) are measured with a preset sampling interval, for example, every 0.1 second. This sampling interval is not limited to 0.1 second.

(Step 7-2)

Figure 28:
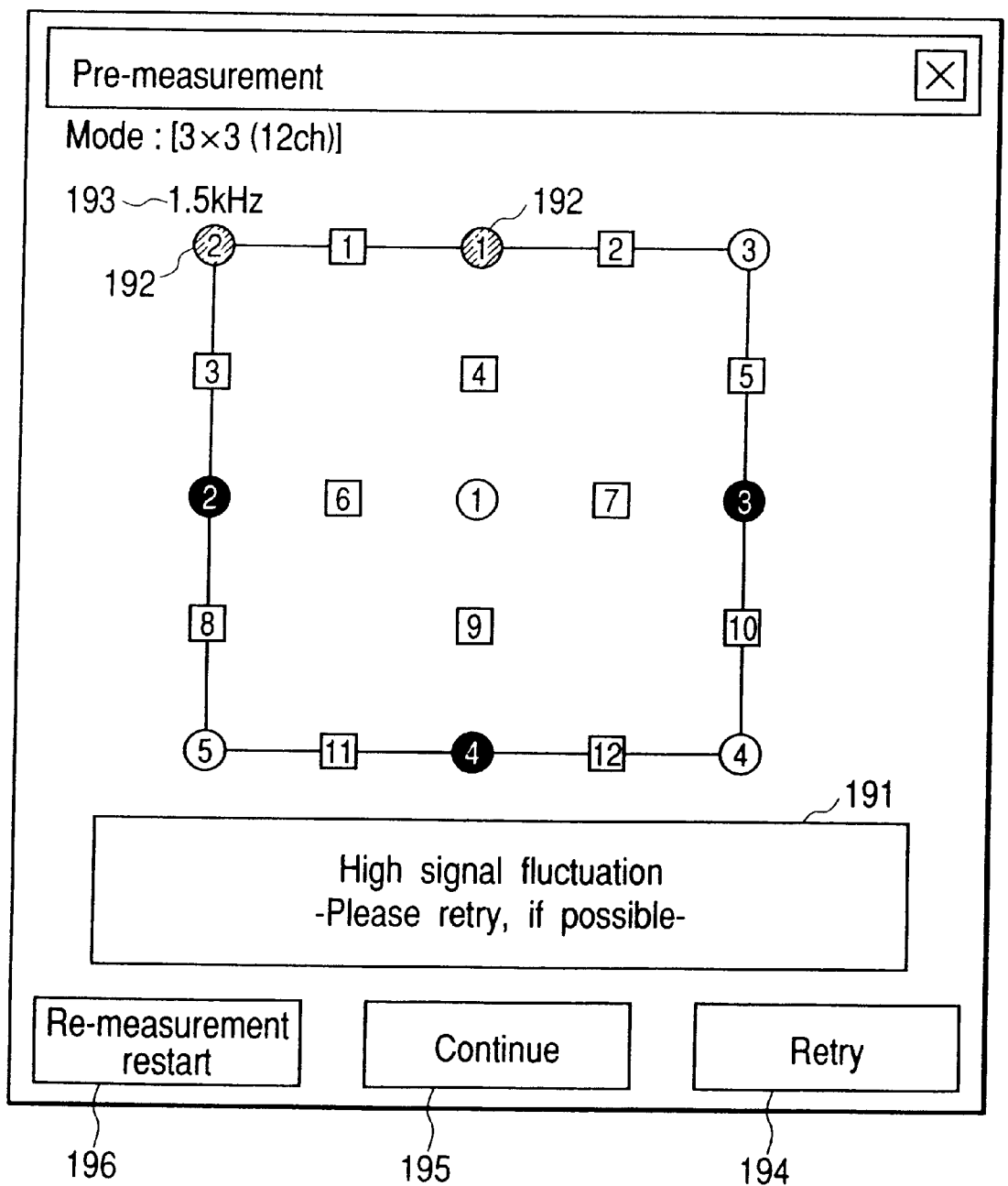
FIG. 28 is a diagram showing a window for displaying a high fluctuation measurement signal during the pre-measurement in the embodiment.

The fluctuation, for example, the standard deviation, of each of the detection signal levels during the selected time period is calculated. If the value of the standard deviation exceeds a fixed range, the incident positions and the detection positions related to the signal are displayed on the display unit 20. FIG. 28 shows an example of such a display. On the displayed picture, it is indicated by letters that the fluctuation of the detection signal level is out of the appropriate range (191), and in the optical fiber position arrangement figure, the background color of the graphic element representing the corresponding incident position and the corresponding detection position is displayed, for example, in yellow. Further, the modulation frequency relating to the signal is also displayed at a position near the corresponding graphic element together (193). When the fluctuation is out of the fixed range, there is a possibility that another apparatus producing a frequency relating to the modulation frequency exists around the optical measurement system in accordance with the present invention. Therefore, the power sources of unnecessary other apparatuses are switched off, and then the Retry button (194) is pushed again to execute the fluctuation measurement of Step 7-1. If the fluctuation is not changed in the retry operation, there is a possibility that the related laser diode, the related photo-detector, the related amplifier or the related lock-in amplifier is faulty, and accordingly should be replaced by a spare device, if necessary.

In that case, if the operator selects the Retry button (196) for the preparation measurement, the processing is returned to Step 1. For example, FIG. 28 shows an example in which hatching is used instead of the yellow background color for the sake of convenience as a case where the detection signal level relating to the "detection position 2" and the "incident position 1" is low and out of the appropriate level (192).

(Step 7-3)

The values of Pv(x, z) and the values of G(x, y, z) are recorded by the recording unit 18.

Thus, the preparation measurement is completed, and the regular measurement can be performed using the values of Pv(x, z) and the values of G(x, y, z). In the preparation measurement described above, the change of the optical intensity level of each of the laser diodes is performed by controlling the applied currents from the oscillator and the drive circuit 4 using the control unit 17. However, the change of the optical intensity level is not limited to the change of the applied currents, but may be performed by introducing a variable light attenuation filter onto the light path from the laser diode to the test object.

Figure 29:
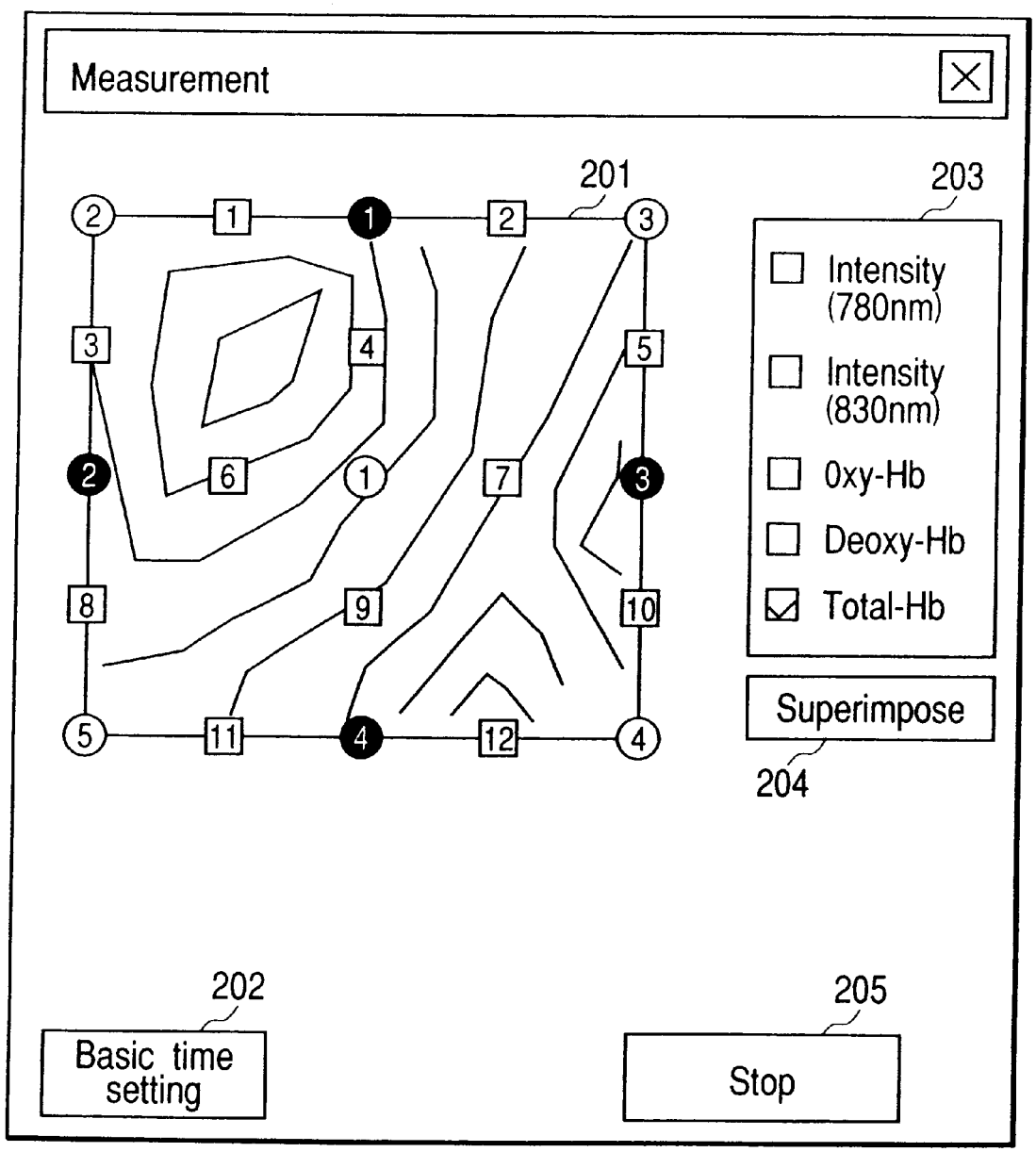
FIG. 29 is a diagram showing a measurement window during regular measurement in the embodiment.
Figure 30:
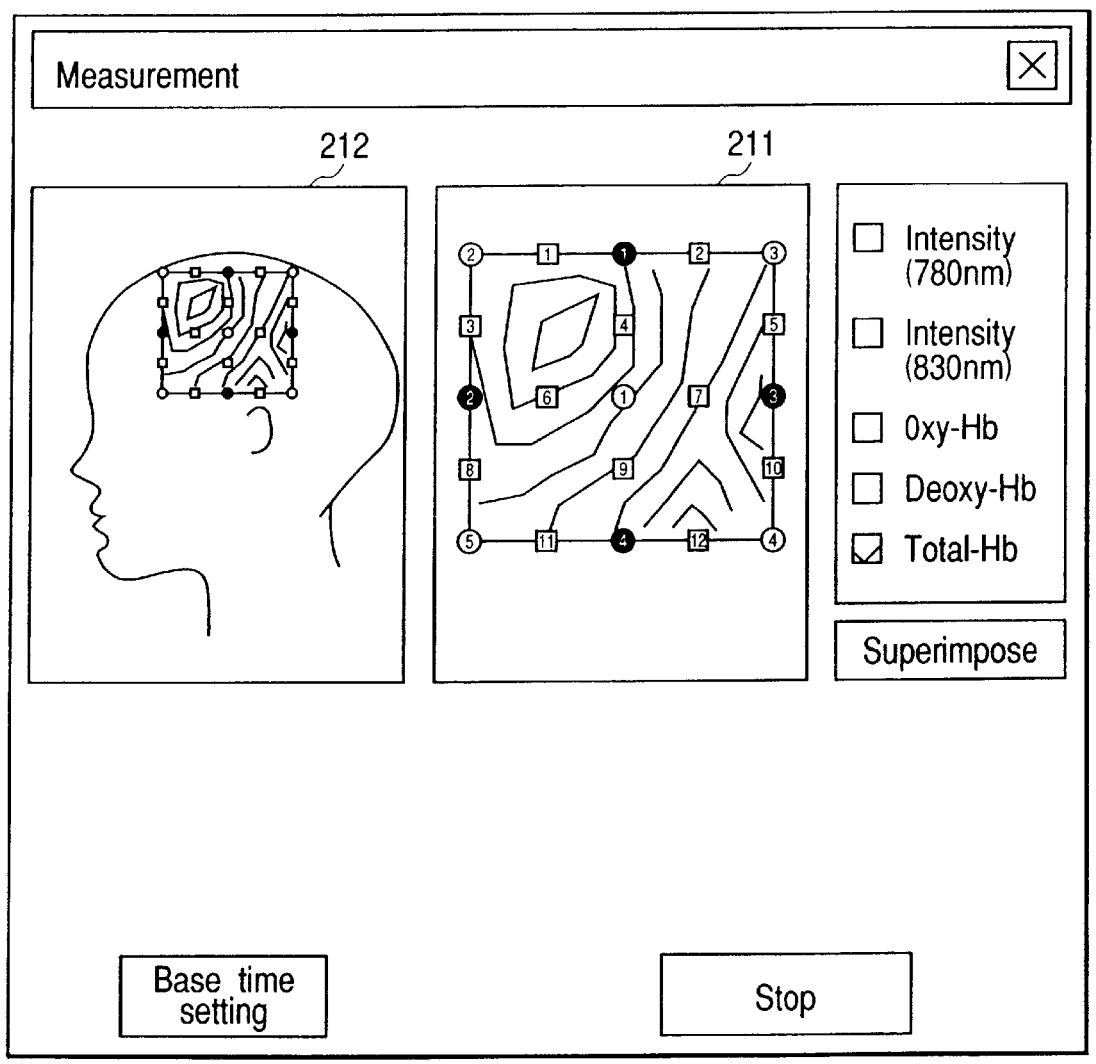
FIG. 30 is a diagram showing an example of a window in the embodiment in which the measurement window during regular measurement and the measurement window overlapped with the outer shape of the test object are displayed.

During the regular measurement, a relative value changing rate for each measurement signal, or concentration changes of oxygenated hemoglobin, deoxygenated hemoglobin and total hemoglobin, are displayed as a topographic image through a real-time or a periodic filtering on the basis of the reference time when the operator selects the Basic time setting button 202, as shown, for example, in the measurement display picture portion (201) in FIG. 29. Which change is to be displayed is performed by selecting an item of the check item display 203. If the display basic time setting button is not selected, the reference time is the time point when the regular measurement is started. Further, by selecting the position superimpose button 204, the incident positions, the detection positions and the measurement positions may be displayed by superposing them on the topographic image. Therein, by selecting the Stop button (205), measurement can be discontinued. Further, as shown in FIG. 30, the measurement image (211) shown in FIG. 29 and the image showing the outer shape of the test object (or the image expressing the inside structure of the test object) and the display (212) superposing the graphic elements of measurement positions on the measurement image may be put side by side.

When the detection signal levels are extremely changed due to a large physiological change in the test object or a sudden mounting displacement of the probe during the regular measurement, this is displayed on the display unit 20 by the following method.

Figure 31:
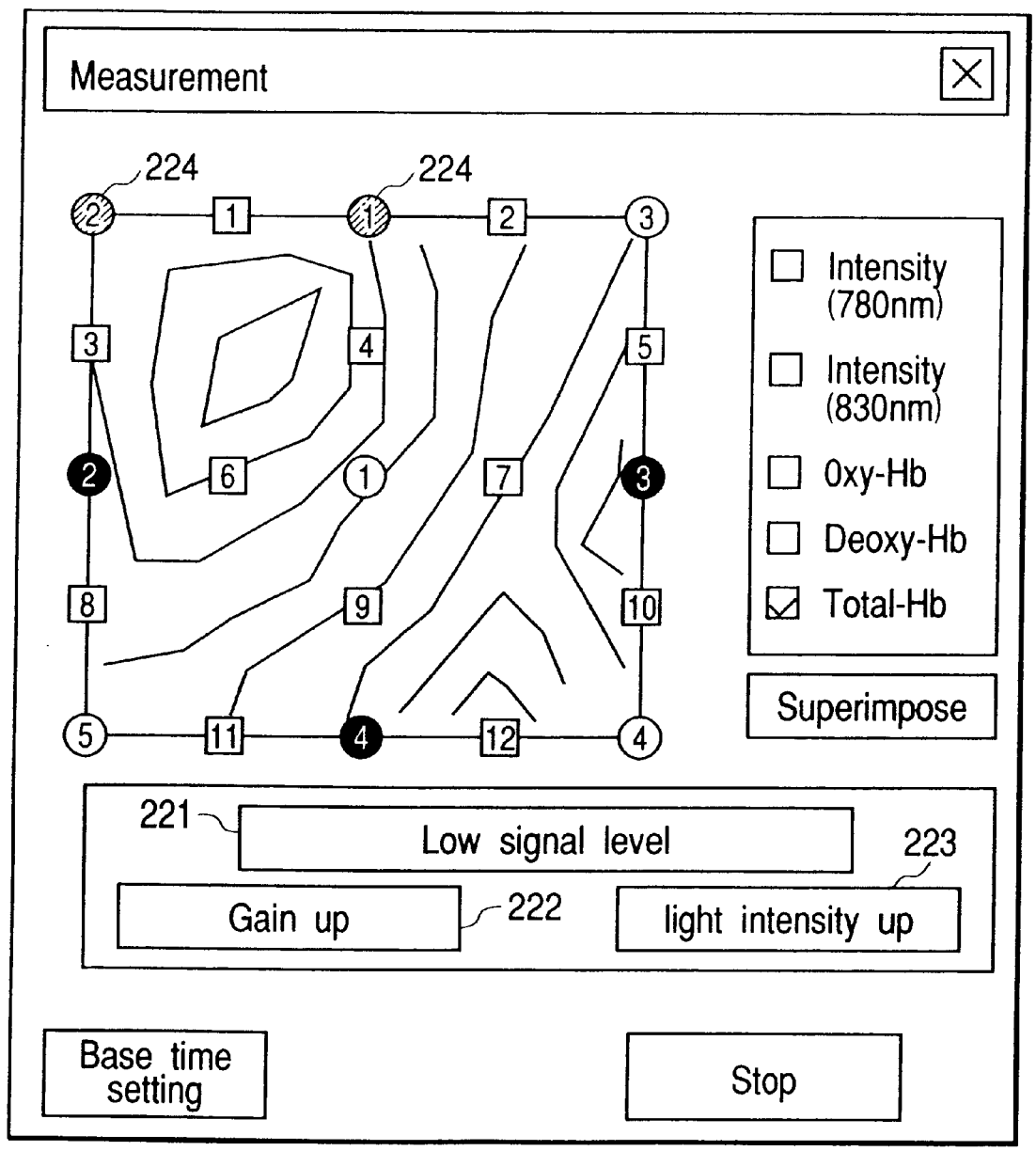
FIG. 31 is a diagram showing a window displaying a low signal level during the regular measurement in the embodiment.

Initially, description will be made of a case where the detection signal level becomes smaller than a set value. Referring to FIG. 31, it is indicated by letters that the signal level is decreased (221), and the background color of the graphic elements representing the corresponding incident positions and the corresponding detection positions and the corresponding measurement positions is changed, for example, to yellow. Even if the display is changed to this state, the regular measurement itself is continued without being affected by this state. When the measurement is intended to be continued while keeping the measurement condition, there is no need to add any new operation. For example, FIG. 31 shows an example in which hatching is used instead of the yellow background color for the sake of convenience as a case where the detection signal level relating to the detection position 2 and the incident position 1 is decreased (224).

Therein, the amplification factors of the amplifiers relating to the corresponding signal are increased by a set increment every time when the Gain up button (222) shown in FIG. 31 is pushed once. Further, the optical intensities of the laser diodes relating to the corresponding signal are increased by a set increment every time when the Light intensity up button (223) shown in FIG. 31 is pushed once. When the detection signal reaches the appropriate level, the letters indicating Low signal level disappear, and the background color of the graphic elements expressing the corresponding incident positions and the corresponding detection positions and the corresponding measurement positions is returned to the original color. Further, every time the Gain up button and the Light intensity up button are pushed, the numbers of the changed signals and the changed values are recorded.

Figure 32:
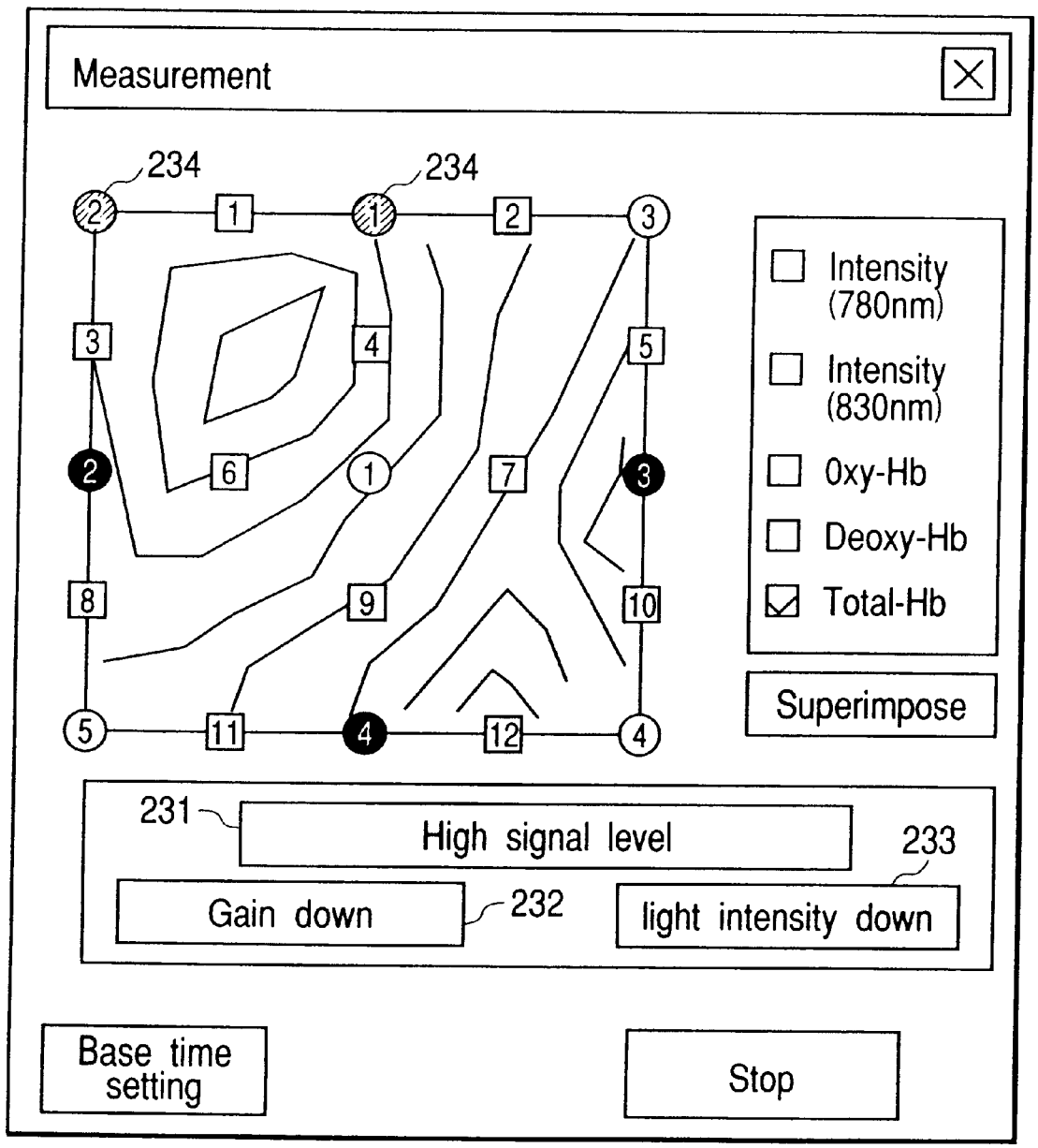
FIG. 32 is a diagram showing a window displaying a high signal level during the regular measurement in the embodiment.

Next, a description will be made of a case where the detection signal level becomes larger than a set value. Referring to FIG. 32, it is indicated by letters that the signal level is increased (231), and the background color of the graphic elements representing the corresponding incident positions and the corresponding detection positions and the corresponding measurement positions is changed, for example, to orange. Even if the display is changed to this state, the regular measurement itself is continued without being affected by this state. When the measurement is intended to be continued while keeping the measurement condition, there is no need to add any new operation. For example, FIG. 32 shows an example in which hatching is used instead of the orange background color for the sake of convenience as a case where the detection signal level relating to the detection position 2 and the incident position 1 is increased (234).

Therein, the amplification factors of the amplifiers relating to the corresponding signal are decreased by a set decrement every time the Gain down button (232) shown in FIG. 31 is pushed once. Further, the optical intensities of the laser diodes relating to the corresponding signal are decreased by a set decrement every time the Light intensity down button (233) shown in FIG. 31 is pushed once. When the detection signal reaches the appropriate level, the letters indicating High signal level disappear, and the background color of the graphic elements representing the corresponding incident positions and the corresponding detection positions and the corresponding measurement positions is returned to the original color. Further, every time the Gain down button and the Light intensity down button are pushed, the numbers of the changed signals and the changed values are recorded. When the state of the orange color light is continuous and the detection signals approach a set signal level, for example, the fixed upper limit of the dynamic range of the analogue-to-digital converter corresponding to the input, the orange color light changed to flashing. When the flashing light is further continued for a set time period, the amplification factors of the amplifiers relating to the corresponding signal level are automatically decreased by a set ratio, for example, by 50%. The changes of the amplification factors and the optical intensities described above and the numbers of the signals and the values which are changed every time the Gain down button and the Light intensity down button are pushed are recorded.

In a case where the detection signal levels are largely changed, the display may be also performed in the corresponding display element in the optical fiber and the probe in addition to the change of the graphic elements in the display unit.

In regard to the display described above relating to the change in the detection signal levels during regular measurement, the displaying method is not limited to the change in the detection signal levels, but the displaying method may be applied to, for example, the change of concentration of a pigment, such as hemoglobin or cytochrome or myoglobin, during regular measurement.

Further, the programs for executing the display and the measurement described in this embodiment are recorded in a computer-readable medium, such as a hard disk, a floppy disk, a CD-ROM or the like. The present invention is not limited by the flow of the preparation measurement shown in the embodiment.

As described above, the optical measurement system and the recording medium and the optical measurement method in accordance with the present invention are implemented by adopting the following functions.

The present invention includes a display unit wherein, in regard to the incident positions of the light on the test object and the detection positions of the light from the test object, or measurement positions determined by spatial arrangement between the incident positions and the detection positions, the display unit displays a relative positional relationship among the positions and a state of the detection signals or a change in the state.

The present invention includes a display unit that displays a state of the detection signals or a change in the state in regard to a plurality of wavelengths.

The incident position and the detection position and the measurement position are shown by graphic elements, and the graphic elements are arranged in a specified pattern.

The scale bar showing a distance between the incident position and the detection position and the measurement position in the test object is displayed.

The state of the detection signals or the change in the state or the fluctuation per unit time of the state is displayed by a color or a pattern or a symbol or a character.

The state of the detection signals or the change in the state or the fluctuation per unit time of the state is displayed by a change in a color or in a pattern of the graphic elements representing the incident positions and the detection positions and the measurement positions.

The graphic elements representing the incident positions and the detecting positions and the measurement positions are superposed on an image indicative of an outer shape or an inner shape of the test object.

The shape of the test object, and information expressing coordinates of the incident positions and the detection positions and the measurement positions in the test object by numerical values are displayed.

The present invention includes optical illuminating means to illuminate the test object; and an optical detection means for detecting light received from the test object; and display elements in probes to mount these means to the test object, and the display elements are operated in an interlocking manner with display of the graphic elements of the display unit.

The state of the detection signal is a detection optical intensity or a state inside the test object.

The state inside the test object is a concentration of hemoglobin or cytochrome or myoglobin, or a change in the concentration.

The graphic element of the incident position or the detection position selected in the display unit is displayed corresponding to the optical illuminating means and to the optical detection means and to the display element in the probe.

Optical fibers are used for the optical illuminating means and the optical detection means, and light emitting elements are included in the optical illuminating means and the optical detection means and the probe.

In regard to the incident positions of the light on the test object and the detection positions of the light from the test object and measurement positions determined by spatial arrangement between the incident positions and the detection positions, a relative positional relationship among the positions is displayed; and, when any one position of the displayed incident positions and the displayed detection positions is specified, an optical fiber set at the corresponding position among incident optical fibers to the test object or detection optical fibers from the test object is identified.

The stray light, in a state before illuminating light to the test object, is detected to measure a stray light signal level, and identification display in regard to the specified stray light signal level is produced for a graphic element representing the detection position.

The light passed through the inside of the test object in response to illuminating light is detected and converted into an electric signal; a detection signal in each of the measurement positions is generated based on the electric signal; a signal level of the detection signal is measured; and identification display is produced for a graphic element representing the incident position or the detection position corresponding to the signal level.

Light having a plurality of wavelengths is individually illuminated on the incident positions; the light which has passed through the inside of the test object in response to the illuminating light is detected and converted into an electric signal; a detection signal for each of the wavelengths in each of the measurement positions is generated based on the electric signal; and identification display is produced for the graphic elements representing the incident positions, the detection positions and the measurement positions.

Identification display is produced for the graphic elements representing the incident positions, the detection positions and the measurement positions corresponding to the measured stray signal levels.

When the stray light signal level is out of an appropriate range, an optical fiber set at the corresponding position among incident optical fibers to the test object or detection optical fibers from the test object is identified.

The plurality of detection levels are independently amplified using individual amplifiers, and an incident optical intensity level for each of the incident positions is independently changed.

The plurality of detection levels are independently amplified using individual amplifiers, and an incident optical intensity level for each of the incident positions and each of the wavelengths is independently changed.

The amplification factors of the amplifiers and the optical intensity levels are changed so that each of the differences between the detection signal levels may fall within an appropriate range.

When the detection signal level is out of an appropriate range, an identification display is produced for the graphic elements representing the corresponding incident position, the corresponding detection position and the corresponding measurement position.

When an amplification factor of the amplifiers or the optical intensity level is out of an appropriate range, an identification display is produced for the graphic elements representing the corresponding incident position, the corresponding detection position and the corresponding measurement position.

When the identification display is produced, an optical fiber set at the corresponding position among the incident optical fibers to the test object or the detection optical fibers from the test object is identified.

The amplification factor of the amplifier in regard to the corresponding detection signal or the optical intensity level of the corresponding incident light is changed with a specified rate.

The value of changing the amplification factor and the optical intensity level and time data corresponding to the time of the change and a number allocated to the changed measurement signal are recorded.

The present invention includes a computer-readable recording medium which records a program for calculating incident positions of the light on the test object and detection positions of the light from the test object, measurement positions determined by spatial arrangement between the incident positions and the detection positions; a program for displaying a relative positional relationship among the incident positions and the detection positions and the measurement positions; and a program for displaying a state of detection signals or a change in the state.

The program for displaying a state of detection signals or a change in the state recorded in the computer-readable recording medium comprises a program for measuring a stray light signal and for specifying the stray light signal level; a program for measuring a detection signal and for specifying the detection signal level; a program for changing a light incident level for each of the incident positions; a program for producing an identification display of graphic elements representing the incident position, the detection position and the measurement position; and a program identifying an optical fiber set at the corresponding position among incident optical fibers to the test object or detection optical fibers from the test object when the identification display is produced.

In the non-invasive imaging measurement method of a biological object using light, in regard to the incident positions of the light to the test object and the detection positions of the light from the test object, or measurement positions determined by spatial arrangement between the incident positions and the detection positions, the method comprises the steps of displaying a relative positional relationship among the positions; specifying any one of a displayed incident position and a displayed detection position; identifying an optical fiber set at the corresponding position among incident optical fibers to the test object or detection optical fibers from the test object; and mounting the identified optical fiber to an appropriate position of the test object.

In a system performing measurement by mounting a large number of optical fibers, an operator can speedily perform the work by correctly judging which optical fiber is to be mounted to which position of the test object.

Further, in a multichannel simultaneous measurement using plural wavelengths and plural positions of high time-resolution, it is possible to provide a high-reliable measurement system, and it is also possible to provide a high-operability system by clearly displaying an optical fiber having a problem and a position of the optical fiber among many mounted optical fibers when the problem occurs in the mounting state of the optical fiber to a test object.

Furthermore, it is possible to provide an efficient measurement system which comprises a mechanism in which the detection signal level is always monitored during actual measurement, and when the detection signal level is about to move out of the dynamic range of the signal input device, the incident positions and the detection positions relating to the detection signal are displayed and the detection signal level is automatically adjusted.

What is claimed is:

1. An optical measurement system for measuring an inside of a test object by illuminating light having a wavelength within a range from visual light to infrared light onto a plurality of incident positions on the test object and detecting the light passed through the inside of the test object at plurality of detection positions, which comprises a display unit which displays graphical elements respectively indicating the incident positions, the detection positions and measurement positions, each of the measurement positions being determined by a spatial arrangement of each of a pair of one of the incident positions and one of said detection positions, wherein positions of the graphical elements on a displayed image are indicative of a relative positional relationship among the incident positions, the detection positions and the measurement positions, and at least one of a color and a pattern of each of the graphical elements is changed according to a state of a detection signal or a change of the state.

2. An optical measurement system according to claim 1, wherein in the display unit, the shape of the test object, and information expressing coordinates of the incident positions and the detection positions and the measurement positions in the test object by numerical values are displayed.

3. An optical measurement system for measuring an inside of a test object by illuminating light having a wavelength within a range from visual light to infrared light onto a plurality of incident positions on the test object and detecting the light passed through the inside of the test object at plurality of detection positions, wherein in regard to the incident positions of the light to the test object and the detection positions of the light from the test object and measurement positions determined by spatial arrangement between the incident positions and the detection positions, a relative positional relationship among the positions is displayed; and when any one position of the displayed incident positions and the displayed detection positions is specified, an optical fiber set at the corresponding position among incident optical fibers to the test object or detection optical fibers from the test object is identified.

4. An optical measurement system for measuring an inside of a test object by illuminating light having a wavelength within a range from visual light to infrared light onto a plurality of incident positions on the test object and detecting the light passed through the inside of the test object at plurality of detection positions, wherein in regard to the incident positions of the light to the test object and the detection positions of the light from the test object and measurement positions determined by spatial arrangement between the incident positions and the detection positions, a relative positional relationship among the positions and a state of detection signals or a change in the state are displayed, and when any one position of the displayed incident positions and the displayed detection positions is specified, an optical fiber set at the corresponding position among incident optical fibers to the test object or detection optical fibers from the test object is identified.

5. An optical measurement system for measuring an inside of a test object by illuminating light having a wavelength within a range from visual light to infrared light onto a plurality of incident positions on the test object and detecting the light passed through the inside of the test object at plurality of detection positions, wherein in regard to the incident positions of the light to the test object and the detection positions of the light from the test object and measurement positions determined by a spatial arrangement between the incident positions and the detection positions, a relative positional relationship among the positions is displayed;

wherein a light level of stray light in a state before illuminating the light to the test object is detected at each of the detection positions, and each of the detection positions is displayed by a graphic element selected according to the light level detected.

6. An optical measurement system according to claim 5, wherein the selected graphical element has a color or a pattern selected according to the detected light level.

7. An optical measurement system for measuring an inside of a test object by illuminating light having a wavelength within a range from visual light to infrared light onto a plurality of incident positions on the test object and detecting the light passed through the inside of the test object at plurality of detection positions, wherein in regard to the incident positions of the light to the test object and the detection positions of the light from the test object and measurement positions determined by a spatial arrangement between the incident positions and the detection positions, a relative positional relationship among the positions is displayed;

wherein a light level of stray light in a state before illuminating the light to the test object is detected at each of the detection positions; and wherein specified detection positions, at which stray light of higher level than a predetermined level is detected, are displayed by a different color or pattern from other detection positions.

8. An optical measurement system for measuring an inside of a test object by illuminating light having a wavelength within a range from visual light to infrared light onto a plurality of incident positions on the test object and detecting the light passed through the inside of the test object at plurality of detection positions, which comprises a display unit which displays graphical elements respectively indicating the incident positions, the detection positions and measurement positions, each of the measurement positions being determined by a spatial arrangement of each of a pair of one of the incident positions and one of the detection positions, a relative positional relationship among the positions is displayed;

wherein positions of the graphical elements on a displayed image are indicative of a relative positional relationship among the incident positions, the detection positions and the measurement positions;

wherein an individual light detection signal level of each of the measurement positions is determined by specifying an effective pair of one of the incident positions and one of the detection positions; and when the light detection signal level is outside of predetermined range, at least one of a color and a pattern of the graphical elements expressing the corresponding incident position, the corresponding detection position, and the corresponding measurement position is changed.

9. An optical measurement system according to claim 8, wherein optical fibers are utilized for illuminating the light to the test object and for detecting the light passed through the inside of the object, and when the detection signal level is outside of the predetermined range, identification display is performed to the graphic elements expressing the corresponding incident position, the corresponding detection position and the corresponding measurement position, and when the identification display is performed, an optical fiber set at the corresponding position among the incident optical fibers to the test object or the detection optical fibers from the test object is identified.

10. A computer-readable recording medium used for a system for measuring an inside of a test object by illuminating light having a wavelength within a range from visual light to infrared light onto a plurality of incident positions on the test object and detecting the light passed through the inside of the test object at plurality of detection positions, which records:

a program for calculating incident positions of the light to the test object and detection positions of the light from the test object, and measurement positions determined by spatial arrangement between the incident positions and the detection positions;

a program for displaying a relative positional relationship among the incident positions and the detection positions and the measurement positions; and a program for displaying a state of detection signals or a change in the state;

wherein said program for displaying a state of detection signals or a change in the state comprises:
  a program for measuring a stray light signal and for specifying the stray light signal level;
  a program for measuring a detection signal and for specifying the detection signal level;
  a program for changing a light incident level for each of the incident positions;
  a program for performing identification display to graphic elements expressing the incident position, the detection position and the measurement position; and
  a program identifying an optical fiber set at the corresponding position among incident optical fibers to the test object or detection optical fibers from the test object when the identification display is performed.

11. A non-invasive imaging measurement method of a biological object using light, wherein in regard to the incident positions of the light to the test object and the detection positions of the light from test object, or measurement positions determined by spatial arrangement between the incident positions and the detection positions, the method comprises the steps of:
  displaying a relative positional relationship among the positions;
  specifying any one of the displayed incident position and the displayed detection position;
  identifying an optical fiber set at the corresponding position among incident optical fibers to the test object or detection optical fibers from the test object; and
  mounting the identified optical fiber to an appropriate position of the test object.

* * * * *